(12) United States Patent  (10) Patent No.: US 6,750,205 B2
Ashley et al.  (45) Date of Patent: *Jun. 15, 2004

(54) MOTILIDE COMPOUNDS

(75) Inventors: Gary Ashley, Alameda, CA (US);
Mark Burlingame, San Francisco, CA (US); Christopher Carreras, Belmont, CA (US); Daniel Santi, San Francisco, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/409,429

(22) Filed: Apr. 7, 2003

(65) Prior Publication Data

US 2003/0220271 A1 Nov. 27, 2003

Related U.S. Application Data

(63) Continuation of application No. 09/788,314, filed on Feb. 15, 2001, now Pat. No. 6,562,795.
(60) Provisional application No. 60/183,338, filed on Feb. 18, 2000.

(51) Int. Cl.$^7$ .......................... A61K 31/70; C07H 17/08
(52) U.S. Cl. ............................ 514/29; 536/7.2; 536/7.4
(58) Field of Search ..................... 514/29; 536/7.2, 536/7.4

(56) References Cited

U.S. PATENT DOCUMENTS

| 4,677,097 A | 6/1987 | Omura et al. .................. 514/29 |
| 4,916,138 A | 4/1990 | Ueda et al. .................. 514/294 |
| 5,523,401 A | 6/1996 | Freiberg et al. ............. 540/457 |

(List continued on next page.)

FOREIGN PATENT DOCUMENTS

| EP | 428169 A | 5/1991 |
| WO | WO 93/13780 | 7/1993 |
| WO | WO 97/02358 | 1/1997 |

(List continued on next page.)

OTHER PUBLICATIONS

Faghih et al., *Drugs of the Future* (1998) 23(8), 861–872.
Honbo et al., *Transplantation Proceedings XIX* (1987), 6 (Supp.), 17–22.
Weber et al., *J. Bacteriol.* (1985) 164 (1), 425–433.

Primary Examiner—Elli Peselev
(74) Attorney, Agent, or Firm—Yuan Chao; Gary W. Ashley

(57) ABSTRACT

The present invention provides novel macrolide compounds of the formulas

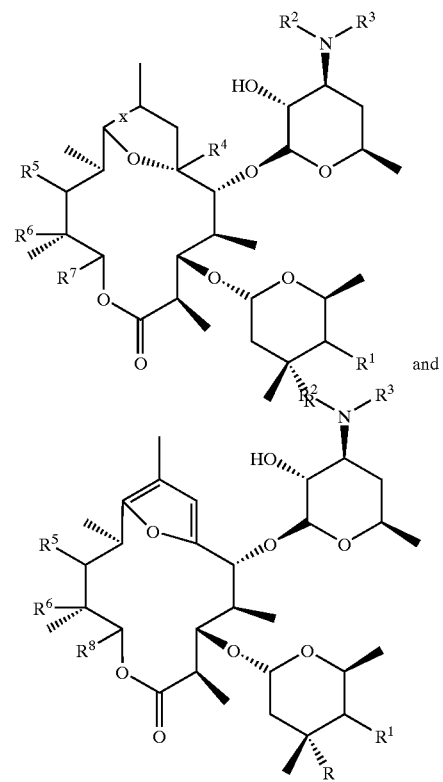

wherein:
R is hydroxyl or methoxy;
$R^1$ is selected from the group consisting of hydrogen, hydroxyl, halide, $NH_2$, $OR^9$,
$$\overset{O}{\underset{}{\|}}\ OCR^9, \quad \overset{O}{\underset{}{\|}}\ OCNR^{10}R^{11}, \quad \overset{O}{\underset{}{\|}}\ NCR^9, \text{ and } \overset{O}{\underset{}{\|}}\ NCNR^{10}R^{11}$$

where $R^9$ is $C_1$–$C_{10}$ alkyl, $C_2$–$C_{10}$ alkenyl, $C_2$–$C_{10}$ alkynyl, aryl or heteroaryl and $R^{10}$ and $R^{11}$ are each independently hydrogen, $C_1$–$C_{10}$ alkyl, $C_2$–$C_{10}$ alkenyl, $C_2$–$C_{10}$ alkynyl, or aryl;

$R^2$ and $R^3$ are each independently selected from the group consisting of hydrogen, $C_1$–$C_{10}$ alkyl, $C_2$–$C_{10}$ alkenyl, $C_2$–$C_{10}$ alkynyl, aryl, alkylaryl, alkenylaryl alkynylaryl or $R^2$ and $R^3$ together form a cycloalkyl or a cycloaryl moiety;

$R^4$ is hydrogen or methyl;
$R^5$ is hydrogen, hydroxyl, oxo, or together with $R^6$ and the carbons to which they are attached form a cyclic carbonate;
$R^6$ is hydrogen, hydroxyl, $OR^{12}$ where $R^{12}$ is $C_1$–$C_{10}$ alkyl, $C_2$–$C_{10}$ alkenyl, $C_2$–$C_{10}$ alkynyl, or together with $R^5$ and the carbons to which they are attached form a cyclic carbonate;
$R^7$ is methyl, $C_3$–$C_{10}$ alkyl, $C_2$–$C_{10}$ alkenyl, $C_2$–$C_{10}$ alkynyl, alkylaryl, alkenylaryl, alkynylaryl, amidoalkylaryl, amidoalkenylaryl, or amidoalkynylaryl;
$R^8$ is $C_1$–$C_{10}$ alkyl, $C_2$–$C_{10}$ alkenyl, $C_2$–$C_{10}$ alkynyl, alkylaryl, alkenylaryl, alkynylaryl, amidoalkylaryl, amidoalkenylaryl, or amidoalkynylaryl; and,
x is a single or a double bond.

6 Claims, No Drawings

U.S. PATENT DOCUMENTS

| | | |
|---|---|---|
| 5,523,418 A | 6/1996 | Freiberg et al. .............. 549/270 |
| 5,538,961 A | 7/1996 | Freiberg et al. .............. 514/183 |
| 5,554,605 A | 9/1996 | Freiberg et al. .............. 514/183 |
| 5,578,579 A | 11/1996 | Lartey et al. ................. 514/29 |
| 5,658,888 A | 8/1997 | Koga et al. .................... 514/29 |
| 5,672,491 A | 9/1997 | Khosla et al. ............... 435/148 |
| 5,712,146 A | 1/1998 | Khosla et al. ......... 435/252.35 |
| 5,712,253 A | 1/1998 | Lartey et al. ................. 514/28 |
| 5,830,750 A | 11/1998 | Khosla et al. ......... 435/252.35 |
| 5,843,718 A | 12/1998 | Khosla et al. .............. 435/69.1 |
| 5,854,407 A | 12/1998 | Harada et al. ............... 536/7.2 |
| 5,922,849 A | 7/1999 | Premchandran et al. ..... 536/7.2 |
| 5,962,290 A | 10/1999 | Khosla et al. ............... 435/183 |
| 6,066,721 A | 5/2000 | Khosla et al. ............. 536/23.1 |
| 6,077,943 A | 6/2000 | Omura et al. ................ 536/7.2 |
| 6,084,079 A | 7/2000 | Keyes et al. ................. 536/7.2 |
| 6,524,841 B1 | 2/2003 | McDaniel et al. ....... 435/252.3 |
| 2002/0094962 A1 | 7/2002 | Ashley et al. ................ 514/28 |

FOREIGN PATENT DOCUMENTS

| | | |
|---|---|---|
| WO | WO 98/01571 | 1/1998 |
| WO | WO 99/03986 | 1/1999 |
| WO | WO 99/35157 | 7/1999 |
| WO | WO 00/20601 | 4/2000 |
| WO | WO 00/26349 | 5/2000 |
| WO | WO 00/44717 | 8/2000 |
| WO | WO 00/62783 | 10/2000 |

MOTILIDE COMPOUNDS

CROSS-REFERENCE TO RELATED APPLICATIONS

This application is a continuation of U.S. application Ser. No. 09/788,314, filed Feb. 15, 2001, now U.S. Pat. No. 6,562,795 B2; which claims the benefit of U.S. Provisional Application No. 60/183,338, filed Feb. 18, 2000; the disclosures of which are incorporated herein by reference.

STATEMENT REGARDING FEDERALLY SPONSORED RESEARCH OR DEVELOPMENT

This invention was made with Government support under SBIR Grant No. 1R43 DK57380-01, awarded by the National Institute of Diabetes, Digestive and Kidney Diseases. The Government has certain rights in this invention.

BACKGROUND

The present invention provides novel prokinetic agents with superior pharmacological and pharmacokinetic properties for the treatment of gastrointestinal motility disorders. The invention relates to the fields of chemistry, medicinal chemistry, medicine, molecular biology, and pharmacology.

Gastrointestinal ("GI") motility regulates the orderly movement of ingested material through the gut to insure adequate absorption of nutrients, electrolytes and fluids. Appropriate transit through the esophagus, stomach, small intestine and colon depends on regional control of intraluminal pressure and several sphincters that regulate forward movement and prevent back-flow of GI contents. The normal GI motility pattern may be impaired by a variety of circumstances including disease and surgery.

Disorders of gastrointestinal motility include, for example, gastroparesis and gastroesophageal reflux disease ("GERD"). Gastroparesis is the delayed emptying of stomach contents. Symptoms of gastroparesis include stomach upset, heartburn, nausea, and vomiting. Acute gastroparesis may be caused by, for example, drugs (e.g., opiates), viral enteritis, and hyperglycemia, and is usually managed by treating the underlying disease rather than the motility disorder. The most common causes of chronic gastroparesis are associated with long standing diabetes or idiopathic pseudo-obstruction, often with so-called "non-ulcer" or "functional" dyspepsia.

GERD refers to the varied clinical manifestations of reflux of stomach and duodenal contents into the esophagus. The most common symptoms are heartburn and dysphasia; blood loss may also occur from esophageal erosion. GERD may be associated with low tone and inappropriate relaxation of the lower esophageal sphincter and occurs with gastroparesis in about 40% of cases. In most cases, GERD appears to be treatable with agents that reduce the release of acidic irritant by the stomach (e.g., Prilosec) or agents that increase the tone of the lower esophageal sphincter (e.g., cisapride). Other examples of disorders whose symptoms include impaired gastrointestinal motility are anorexia, gall bladder stasis, postoperative paralytic ileus, scleroderma, intestinal pseudoobstruction, gastritis, emesis, and chronic constipation (colonic inertia).

These GI disorders are generally treated with prokinetic agents that enhance propulsive motility. Motilides are macrolide compounds such as erythromycin and its derivatives that are agonists of the motilin receptor. Evidence of the potential clinical utility of motilides includes their ability to induce phase III of Migrating Motor Complexes ("MMC"). MMC refers to the four phases (I–IV) of electrical activity displayed by the stomach and small intestine in the fasting state. Muscular contraction occurs in phases III and IV which coincide with a peristaltic wave that propels enteric contents distally during fasting. Other clinically relevant effects include: increase in esophageal peristalsis and LES pressure in normal volunteers and patients with GERD; acceleration of gastric emptying in patients with gastric paresis; and stimulation of gallbladder contractions in normal volunteers, patients after gallstone removal, and diabetics with autonomic neuropathy.

The discovery of motilides was serendipitous. Since the 1950's, erythromycin A 1 has been known to cause GI side effects such as nausea, vomiting, and abdominal discomfort. These effects are now largely explained by the motilin agonist activity of erythromycin A and an acid catalyzed degradation production, 8,9-anhydro-6,9-hemiacetal 2, which is also known as the enol ether form.

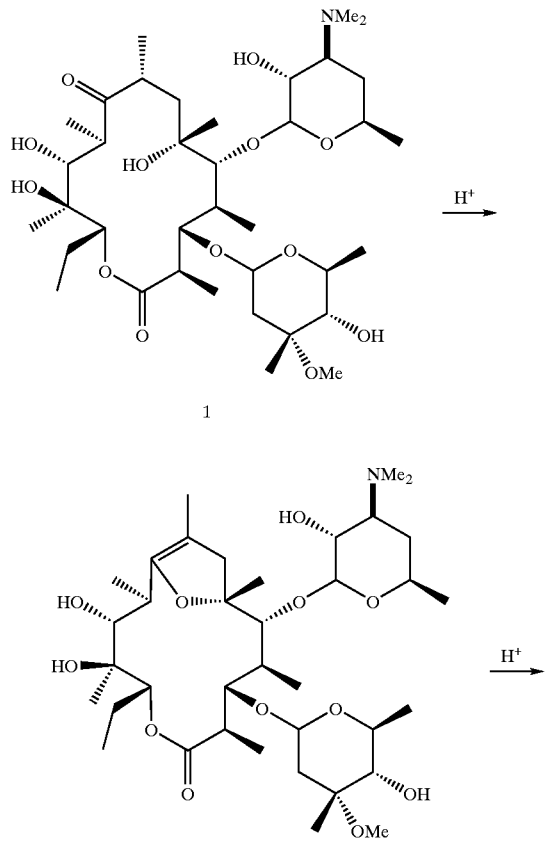

SCHEME A

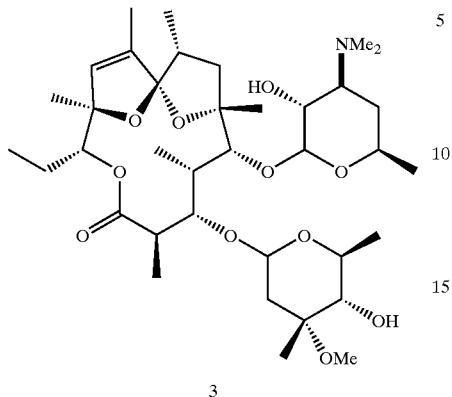

3

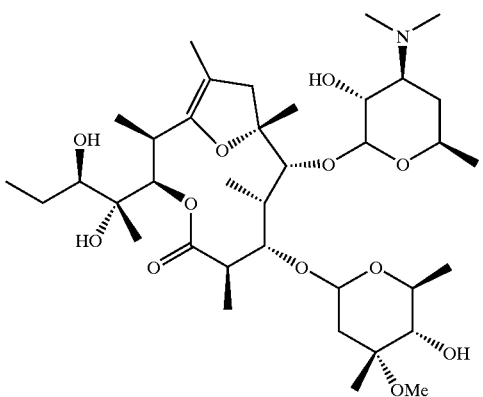

6

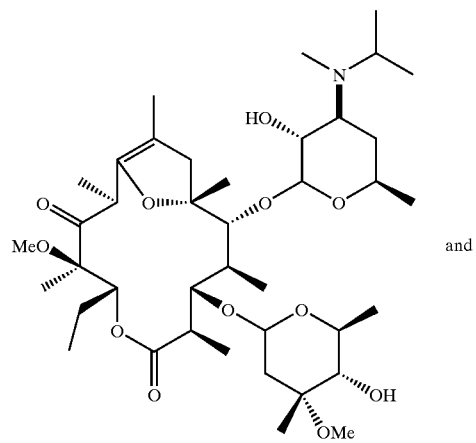

7 and

As illustrated by Scheme A, erythromycin A 1 undergoes an acid catalyzed rearrangement in the stomach to form the enol ether 2 which is then further degraded into the spiroketal 3. Both erythromycin A and the enol ether are motilin agonists but the spiroketal is not. Because the enol ether is approximately ten fold more potent as a motilin agonist than erythromycin A and does not also possess antimicrobial activity, the potential clinical uses of enol ether derivatives as prokinetic agents are being investigated.

Enol ether erythromycin derivatives under clinical investigation include EM-523 (4); EM-574 (5); LY267,108 (6); GM-611 (7); and ABT-229 (8) whose structures are shown below. See U.S. Pat. Nos. 5,578,579; 5,658,888; 5,922,849; 6,077,943; and 6,084,079 which are all incorporated herein by reference.

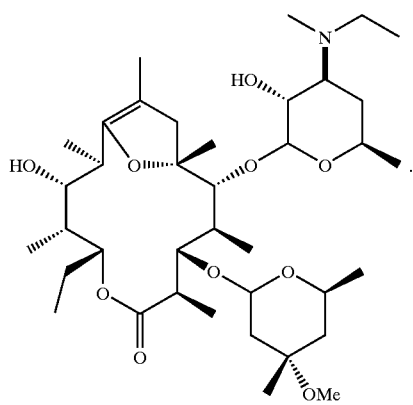

8

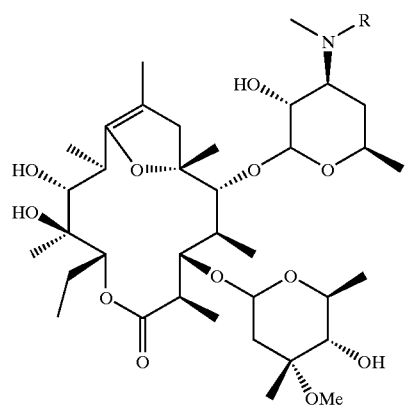

4: R = ethyl
5: R = isopropyl

Other motilides of potential interest include lactam enol ethers and lactam epoxide derivatives. See also U.S. Pat. Nos. 5,712,253; 5,523,401; 5,523,418; 5,538,961; 5,554,605 which are incorporated herein by reference.

In general, these and other previously disclosed macrolides are synthetically accessible compounds that are derived from erythromycin A or B. Because nature has not optimized the erythromycin structure for its prokinetic activity, it is likely that the potency of motilide agonists could be greatly enhanced. Compounds resulting from such efforts could be of significant benefit in the treatment of wide variety of diseases and conditions. The present invention provides such compounds.

SUMMARY

The present invention provides novel macrolide compounds with superior pharmacological and pharmacokinetic properties for the treatment of gastrointestinal motility disorders. In one embodiment, the present invention provides compounds of the formulas

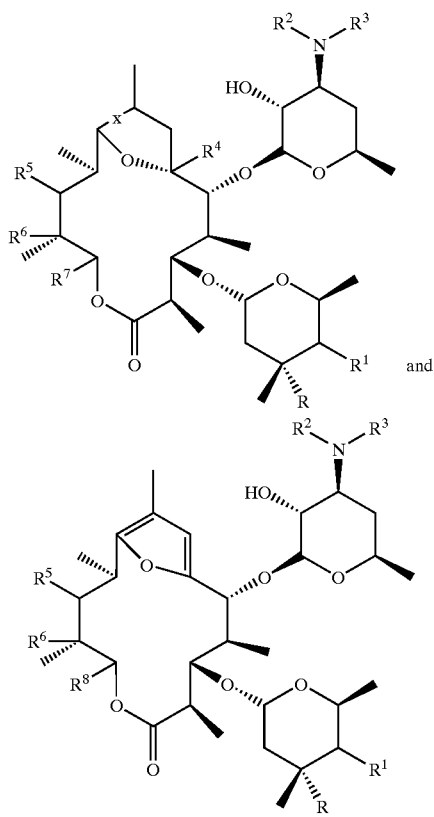

wherein:

R is hydrogen or hydroxyl;

$R^1$ is selected from the group consisting of hydrogen, hydroxyl, halide, $NH_2$, $OR^9$,

where $R^9$ is $C_1$–$C_{10}$ alkyl, $C_2$–$C_{10}$ alkenyl, $C_2$–$C_{10}$ alkynyl, aryl or heteroaryl and $R^{10}$ and $R^{11}$ are each independently hydrogen, $C_1$–$C_{10}$ alkyl, $C_2$–$C_{10}$ alkenyl, $C_2$–$C_{10}$ alkynyl, or aryl;

$R^2$ and $R^3$ are each independently selected from the group consisting of hydrogen, $C_1$–$C_{10}$ alkyl, $C_2$–$C_{10}$ alkenyl, $C_2$–$C_{10}$ alkynyl, aryl, alkylaryl, alkenylaryl, alkynylaryl or $R^2$ and $R^3$ together form a cycloalkyl or a cycloaryl moiety;

$R^4$ is hydrogen or methyl;

$R^5$ is hydrogen, hydroxyl, oxo, or together with $R^6$ and the carbons to which they are attached form a cyclic carbonate;

$R^6$ is hydrogen, hydroxyl, $OR^{12}$ where $R^{12}$ is $C_1$–$C_{10}$ alkyl, $C_2$–$C_{10}$ alkenyl, $C_2$–$C_{10}$ alkynyl, or together with $R^5$ and the carbons to which they are attached form a cyclic carbonate;

$R^7$ is methyl, $C_3$–$C_{10}$ alkyl, $C_2$–$C_{10}$ alkenyl, $C_2$–$C_{10}$ alkynyl, alkylaryl, alkenylaryl, alkynylaryl, amidoalkylaryl, amidoalkenylaryl, or amidoalkynylaryl;

$R^8$ is $C_1$–$C_{10}$ alkyl, $C_2$–$C_{10}$ alkenyl, $C_2$–$C_{10}$ alkynyl, alkylaryl, alkenylaryl, alkynylaryl, amidoalkylaryl, amidoalkenylaryl, or amidoalkynylaryl; and, x is a single or a double bond. These and other embodiments, modes, and aspects of the invention are described in more detail in the following description, the examples, and claims set forth below.

DESCRIPTION OF THE PREFERRED EMBODIMENTS

The present invention provides novel macrolide compounds with superior pharmacological and pharmacokinetic properties for the treatment of gastrointestinal disorders where enhanced GI motiliy is indicated or desired. The compounds of the present invention typically are derived from "unnatural" erythromycins and generally differ from naturally occurring erythromycins A, B, C, and D by having a non-ethyl group (e.g., a group that is not —$CH_2CH_3$) or a substituted ethyl at C-13 and/or by having a hydrogen instead of the methyl group at C-6 (C-6 desmethyl compounds).

Definitions

Many of the inventive compounds contain one or more chiral centers. All of the stereoisomers are included within the scope of the invention, as pure compounds as well as mixtures of stereoisomers. Similarly, all geometric isomers are also included within the scope of the invention. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, flimarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tarnate, tartrate, teoclate, tosylate, triethiodide and valerate.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Listed below are definitions of various terms used to describe this invention. These definitions apply to the terms as they are used throughout this specification, unless otherwise limited in specific instances, either individually or as part of a larger group.

The term "alkyl" refers to an optionally substituted straight, branched or cyclic hydrocarbons. "Alkenyl" refers to an optionally substituted straight, branched, or cyclic chain hydrocarbon with at least one carbon-carbon double bond. "Alkynyl" refers to an optionally substituted straight, branched, or cyclic hydrocarbon with at least one carbon-carbon triple bound. Substituted alkyl, substituted alkenyl, or substituted alkynyl refer to the respective alkyl, alkenyl or alkynyl group substituted by one or more substituents. Illustrative examples of substituents include but are not limited to alkyl alkenyl, alkynyl, aryl, halo; trifluoromethyl; trifluoromethoxy; hydroxy; alkoxy; cycloalkoxy; heterocyclooxy; oxo (=O); alkanoyl (—C(=O)-alkyl); aryloxy; alkanoyloxy; amino; alkylamino; arylamino; aralkylamino; cycloalkylamino; heterocycloamino; disubstituted amines in which the two amino substituents are selected from alkyl, aryl, or aralkyl; alkanoylamino; aroylamino; aralkanoylamino; substituted alkanoylamino; substituted arylamino; substituted aralkanoylamino; thiol; alkylthio; arylthio; aralkylthio; cycloalkylthio; heterocyclothio; alkylthiono; arylthiono; aralkylthiono; alkylsulfonyl; arylsulfonyl; aralkylsulfonyl; sulfonamido (e.g., $SO_2NH_2$); substituted sulfonamido; nitro; cyano; carboxy; carbamyl (e.g., $CONH_2$); substituted carbamyl (e.g., —C(=O)NR'R" where R' and R" are each independently hydrogen, alkyl, aryl, aralkyl and the like); alkoxycarbonyl, aryl, guanidino, and heterocyclo such as indoyl, imidazolyl, furyl, thienyl, thiazolyl, pyrrolidyl, pyridyl, pyrimidyl and the like. Where applicable, the substituent may be further substituted such as with halogen, alkyl, alkoxy, aryl, or aralkyl and the like.

The term "aryl" refers to an optionally substituted aromatic ring having 6 to 12 carbon atoms and may include one or more heteroatoms such as N, S and O. Illustrative examples of aryl include but are not limited to biphenyl, furyl, imidazolyl, indolyl, isoquinolyl, naphthyl, oxazolyl, phenyl, pyridyl, pyrryl, quinolyl, quinoxalyl, tetrazoyl, thiazoyl, thienyl and the like. Substituted aryl refers to an aryl group substituted by, for example, one to four substituents such as substituted and unsubstituted alkyl, alkenyl, alkynyl, and aryl; halo; trifluoromethoxy; trifluoromethyl; hydroxy; alkoxy; cycloalkyloxy; heterocyclooxy; alkanoyl; alkanoyloxy; amino; alkylamino; aralkylamino; cycloalkylamino; heterocycloamino; dialkylamino; alkanoylamino; thio; alkylthio; cycloalkylthio; heterocyclothio; ureido; nitro; cyano; carboxy; carboxyalkyl; carbamyl; alkoxycarbonyl; alkylthiono; arylthiono; alkylsulfonyl; sulfonamido; aryloxy; and the like. The substituent may be further substituted, for example, by halo, hydroxy; alkyl, alkoxy; aryl, substituted aryl, substituted alkyl, substituted aralkyl, and the like.

The terms "alkylaryl" or "arylalkyl" refer to an aryl group bonded directly through an alkyl group, such as benzyl. Similarly, "alkenylaryl" and "arylalkenyl" refer to an aryl group bonded directly through an alkenyl group and "alkynylaryl" and "arylalkynyl" refer to an aryl group bonded directly through an alkynyl group.

The term amidoalkylaryl refer to a group of the formula —ZNH—(C=O)—R'-R" where Z may be present or absent, and Z and R' are each independently an optionally substituted $C_1$–$C_{10}$ alkyl, alkenyl, or alkynyl and R" is an optionally substituted aryl.

The terms "halogen," "halo", or "halide" refer to fluorine, chlorine, bromine and iodine.

The term "erythromycin" refers to a compound of the formula

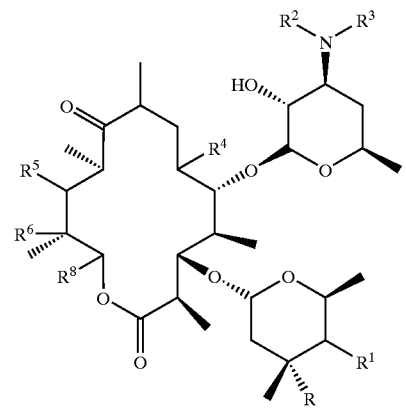

where R, $R^1$, $R^2$, $R^3$, $R^4$, $R^5$, $R^6$, and $R^8$ are as described herein and derivatives and analogs thereof.

Free hydroxyl groups in the compounds of the present invention may optionally be protected with a hydroxyl protecting group. The term "hydroxy protecting group" refers to groups known in the art for such purpose. Commonly used hydroxy protecting groups are disclosed, for example, in T. H. Greene and P. G. M. Wuts, Protective Groups in Organic Synthesis, $2^{nd}$ edition, John Wiley & Sons, New York (1991), which is incorporated herein by reference. Illustrative hydroxyl protecting groups include but not limited to tetrahydropyranyl; benzyl; methylthiomethyl; ethythiomethyl; pivaloyl; phenylsulfonyl; triphenylmethyl; trisubstituted silyl such as trimethyl silyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl and the like; acyl and aroyl such as acetyl, pivaloylbenzoyl, 4-methoxybenzoyl, 4-nitrobenzoyl and aliphatic acylaryl and the like. Hydroxyl protected versions of the inventive compounds are also encompassed within the scope of the present invention.

In addition to the explicit substitutions at the above-described groups, the inventive compounds may include other substitutions where applicable. For example, the erythromycin backbone or backbone substituents may be additionally substituted (e.g., by replacing one of the hydrogens or by derivatizing a non-hydrogen group) with one or more substituents such as $C_1-C_5$ alkyl, $C_1-C_5$ alkoxy, phenyl, or a functional group. Illustrative examples of suitable functional groups include but are not limited to alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, hydrazide, enamine, sulfone, sulfide, sulfenyl, and halogen.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Compounds of the Present Invention

In one embodiment, the present invention provides compounds of the formulas

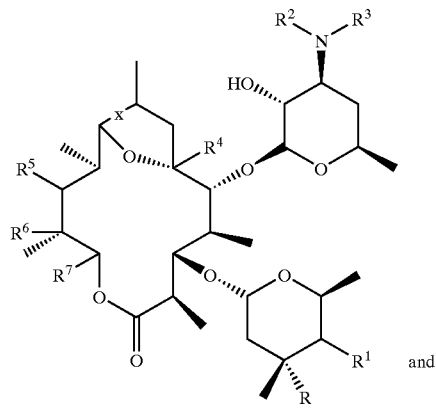

I and II wherein:

R is hydroxyl or methoxy;

$R^1$ is selected from the group consisting of hydrogen, hydroxyl, halide, $NH_2$, $OR^9$, $$\overset{O}{\underset{}{\parallel}}\!\!OCR^9, \quad \overset{O}{\underset{}{\parallel}}\!\!OCNR^{10}R^{11}, \quad \overset{O}{\underset{}{\parallel}}\!\!NCR^9, \text{ and } \overset{O}{\underset{}{\parallel}}\!\!NCNR^{10}R^{11}$$

where $R^9$ is $C_1-C_{10}$ alkyl, $C_2-C_{10}$ alkenyl, $C_2-C_{10}$ alkynyl, aryl or heteroaryl and $R^{10}$ and $R^{11}$ are each independently hydrogen, $C_1-C_{10}$ alkyl, $C_2-C_{10}$ alkenyl, $C_2-C_{10}$ alkynyl, or aryl;

$R^2$ and $R^3$ are each independently selected from the group consisting of hydrogen, $C_1-C_{10}$ alkyl, $C_2-C_{10}$ alkenyl, $C_2-C_{10}$ alkynyl, aryl, alkylaryl, alkenylaryl, alkynylaryl or $R^2$ and $R^3$ together form a cycloalkyl or a cycloaryl moiety;

$R^4$ is hydrogen or methyl;

$R^5$ is hydrogen, hydroxyl, oxo, or together with $R^6$ and the carbons to which they are attached form a cyclic carbonate;

$R^6$ is hydrogen, hydroxyl, $OR^{12}$ where $R^{12}$ is $C_1-C_{10}$ alkyl, $C_2-C_{10}$ alkenyl, $C_2-C_{10}$ alkynyl, or together with $R^5$ and the carbons to which they are attached form a cyclic carbonate;

$R^7$ is methyl, $C_3-C_{10}$ alkyl, $C_2-C_{10}$ alkenyl, $C_2-C_{10}$ alkynyl, alkylaryl, alkenylaryl, alkynylaryl, amidoalkylaryl, amidoalkenylaryl, or amidoalkynylaryl;

$R^8$ is $C_1-C_{10}$ alkyl, $C_2-C_{10}$ alkenyl, $C_2-C_{10}$ alkynyl, alkylaryl, alkenylaryl, alkynylaryl, amidoalkylaryl, amidoalkenylaryl, or amidoalkynylaryl; and, x is a single or a double bond.

In another embodiment, the present invention provides compounds of the formulas

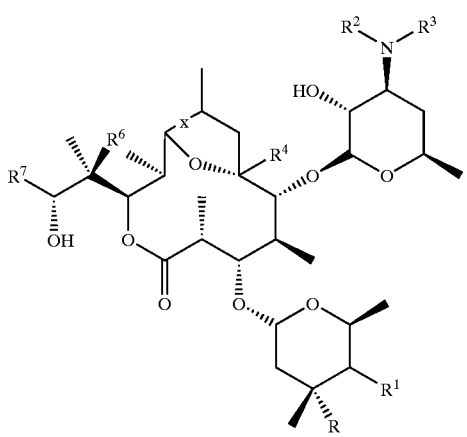

III

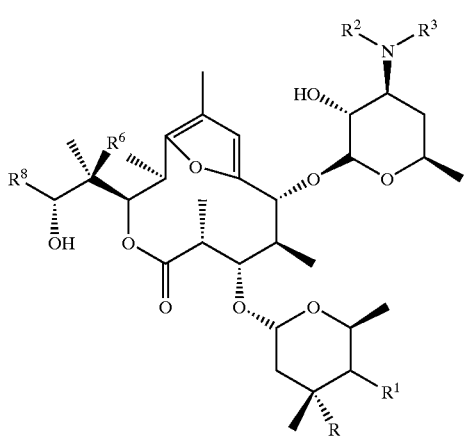

IV wherein R, $R^1$, $R^2$, $R^3$, $R^4$, $R^6$, $R^7$, $R^8$ and x are as described previously.

In another embodiment, the present invention provides compounds of the formulas I, II, III, and IV wherein: R is hydroxyl or methoxy; $R^1$ is hydrogen, hydroxyl, fluoro; $R^2$ and $R^3$ are each independently $C_1$–$C_5$ alkyl, phenyl or benzyl; $R^4$ is methyl; $R^5$ is hydrogen, hydroxyl or oxo; $R^6$ is hydrogen, hydroxyl, or $C_1$–$C_5$ alkoxy; $R^7$ is methyl, $C_3$–$C_5$ alkyl, $C_2$–$C_5$ alkenyl, $C_2$–$C_5$ alkynyl, aryl, alkylaryl or alkenylaryl; $R^8$ is $C_1$–$C_5$ alkyl, $C_2$–$C_5$ alkenyl, $C_2$–$C_5$ alkynyl, aryl, alkylaryl or alkenylaryl; and, x is single bond or a double bond.

In another embodiment, the present invention provides compounds of the formulas I, II, III, and IV wherein: R is hydroxyl or methoxy; $R^1$ is hydrogen or hydroxyl; $R^2$ is methyl; $R^3$ is methyl, ethyl, propyl, isopropyl, butyl, isobutyl, secbutyl, or tertbutyl; $R^4$ is methyl; $R^5$ is hydrogen, hydroxyl or oxo; $R^6$ is hydrogen, hydroxyl, or methoxy; $R^7$ is methyl, vinyl, propyl, isobutyl, pentyl, prop-2-enyl, propargyl, but-3-enyl, 2-azidoethyl, 2-fluoroethyl, 2-chloroethyl, cyclohexyl, phenyl, or benzyl; $R^8$ is methyl, ethyl vinyl, propyl, isobutyl, pentyl, prop-2-enyl, propargyl, but-3-enyl, 2-azidoethyl, 2-fluoroethyl, 2-chloroethyl, cyclohexyl, phenyl, or benzyl; and, x is a single or a double bond.

In another embodiment, the present invention provides compounds of the formulas I, II, III, and IV wherein: R is methoxy; $R^1$ is hydrogen or hydroxyl; $R^2$ is methyl; $R^3$ is methyl, ethyl, or isopropyl; $R^4$ is methyl; $R^5$ is hydrogen, hydroxyl or oxo; $R^6$ is hydrogen, hydroxyl, or methoxy; $R^7$ is propyl, but-3-enyl, 2-azidoethyl, phenyl, or benzyl; $R^8$ is ethyl, propyl, but-3-enyl, 2-azidoethyl, phenyl, or benzyl; and, x is a single or a double bond.

In another embodiment, the present invention provides compounds of the following formulas

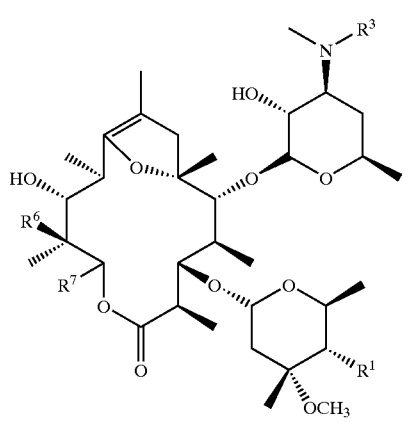

V

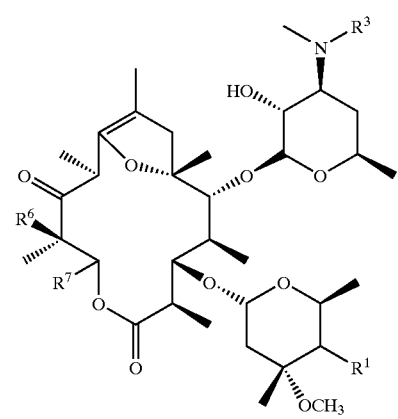

VI

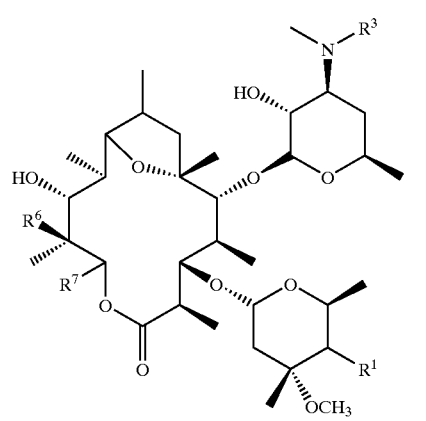

VII and

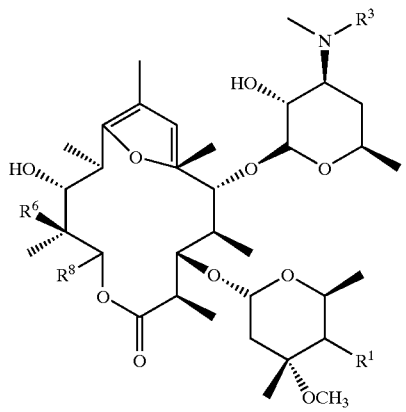

VIII wherein R¹ is hydrogen or hydroxyl; R³ is methyl, ethyl, or isopropyl; R⁶ is hydrogen, hydroxyl, or methoxy; R⁷ is propyl; and R⁹ is ethyl or propyl.

In another embodiment, the present invention provides compounds of the following formulas

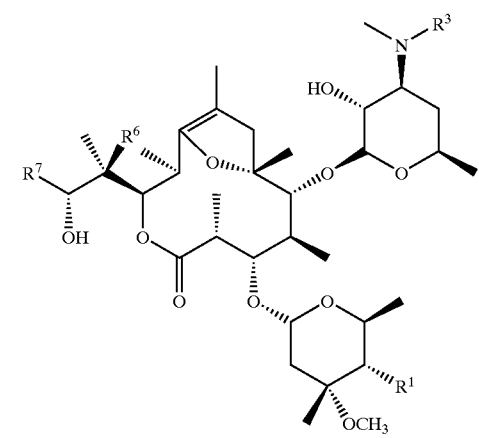

IX

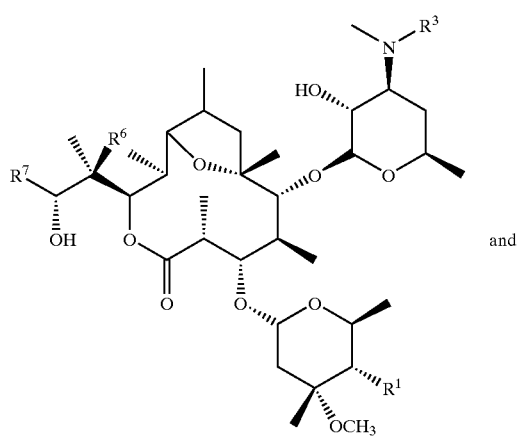

X and

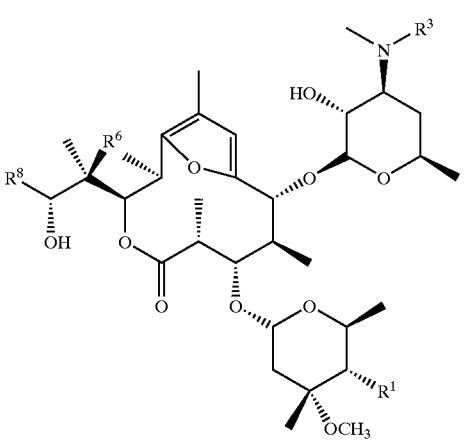

XI wherein R¹ is hydrogen or hydroxyl; R³ is methyl, ethyl, or isopropyl; R⁶ is hydrogen, hydroxyl; R⁷ is propyl; and R⁸ is ethyl or propyl.

Starting Materials

The compounds of the present invention can be prepared in accordance with the methods of the present invention by a combination of recombinant DNA technology and organic chemistry.

Recombinant techniques are used to provide, in many instances, "unnatural" erythromycins or erythromycin derivatives that differ in one or more positions from the naturally occurring erythromycins A, B, C, or D. Although any suitable recombinant means may be used, a useful starting point is the complete 6-dEB synthase gene cluster that has been cloned in vectors and thus is amenable to genetic manipulations in *E. coli* and expression of the polyketide in Streptomyces. See U.S. Pat. Nos. 5,672,491; 5,830,750; 5,843,718; 5,712,146; and 5,962,290 which are all incorporated herein by reference. Once the aglycone is formed, it is next hydroxylated and/or glycoslyated and/or methylated at the appropriate positions by a converter strain that possesses the desired functionalities.

A particularly useful converter strain is an *Saccharopolyspora erythraea* eryA mutant that is unable to produce 6-dEB but can still carry out the desired conversions (Weber et al., J. Bacteriol. 164(1): 425–433 (1985). This mutant strain is able to take exogenously supplied 6-dEB and process it to erythromycin A by converting it into erythronolide B, 3-α-mycarosylerythronolide B, erythromycin D, erythromycin C, and finally to erythromycin A. An alternative route to erythromycin A is through erythromycin B where exogenously supplied 6-dEB is converted into erythronolide B, 3-α-mycarosylerythronolide B, erythromycin D, erythromycin B, and finally to erythromycin A. Other mutant strain, such as eryB, eryC, eryG, and/or eryK mutants, or mutant strains having mutations in multiple genes can be used to make compounds having any combinations of hydroxylations at C-6 and C-12, glycosylations at C-3 and C-5, and methylation at C-3"—OH. Any of these products may be used as starting materials for the practice of the present invention.

Erythromycins where the substituent at C-13 is methyl or ethyl, the 6-deoxyerythronolide B synthase ("DEBS") from *S. erythraea* can be used in a recombinant expression system described in U.S. Pat. No. 5,672,491 to produce the aglycone in *Streptomyces coelicolor*. Optionally, the oleandolide or megalomicin polyketide synthase ("PKS") genes may be used in this expression system. See U.S. Provisional Patent Application Serial No. 60/158,305 filed Oct. 8, 1999 and utility application Ser. No. 09/679,279, filed Oct. 4, 2000, entitled Recombinant Megalomicin Biosynthetic Genes by inventors Robert McDaniel and Yana Volchegursky; and PCT Publication No. WO 00/026,349 which are all incorporated herein by reference.

For erythromycins where the substituent at C-13 is something other than methyl or ethyl, one can employ a technique known as chemobiosynthesis in which activated thioesters called SNAC-diketides are converted to 13-substituted 6-dEB derivatives (13-R-13-desethyl-6-dEB compounds) by fermentation of S. coelicolor CH999/pJRJ2 or functionally similar strains that contain a PKS in which the ketosynthase domain of module 1 has been inactivated by mutation (the KS1° mutation). This methodology is described in PCT Publication Nos. WO 97/02358 and WO 99/03986 and U.S. Pat. No. 6,066,721 which are all incorporated herein by reference. Additional SNAC-diketide compounds and the corresponding aglycones are described in PCT Publication No. WO 00/44717 which is incorporated herein by reference.

6-dEB and 6-dEB derivatives such as 13-substituted 6-dEB are converted into the desired erythromycin starting material by an appropriate converter strain. For example, any one of the post PKS products may be used as starting materials such as 13-substituted counterparts (where the ethyl group which normally exists at C-13 is replaced with another substituent) to: erythronolide B, 3-α-mycarosylerythronolide B, erythromycin D, erythromycin B, erythromycin C, and erythromycin A. In particular, 13-substituted erythromycin A can be made by fermentation with an eryA mutant that is incapable of producing 6-dEB but can still carry out the desired conversions. 13-substituted erythromycin B can be made by fermentation with an eryA mutant that is incapable of producing 6-dEB and in which the ery K (12-hydroxylase) gene has been deleted or otherwise rendered inactive. Alternatively, erythromycin B derivatives can be made in a KS1°/eryK mutant strain of S. erythaea. The general method for using chemobiosynthesis for making modified 6-dEB is illustrated by Example 1 with specific reference to 13-propyl-6-dEB (13-propyl-13-desethyl-6-dEB). The general method for converting modified 6-dEB compounds to the desired hydroxylated and glycosylated form by using an eryA converter strain is illustrated by Example 2 with specific reference to converting 13-propyl 6-dEB to 13-propyl erythromycin A (13-propyl-13-desethyl-erythromycin A).

6-Desmethyl erythromycins, a starting material for making the furanyl erythromycins (compounds of formula II or IV) of the present invention, are made by replacing the acyl transferase ("AT") domain of module 4 (encoding a 6-methyl group) of a 6-dEB or 8,8a-deoxyoleandolide synthase with an AT a malonyl specific AT domain (encoding a 6-hydrogen) to provide the 6-desmethyl analog of the erythromycin aglycone. Illustrative examples of malonyl specific AT domains include AT2 and AT12 of rapamycin; AT3 and AT4 of epothilone; and AT10 of FK-520.

Alternatively, the AT4 domain of 6-dEB or 8,8a-deoxyoleandolide polyketide synthase is mutated to correspond to AT domains more characteristic of AT domains having malonyl specificity. More particularly, three mutations are made. In the first, nucleotides 6214–6227 of the open reading frame encoding AT4 (CGC GTC GAC GTG CTC) is modified to the sequence, GAC GAC CTC TAC GCC where bold indicates the altered nucleotide, to change the encoded amino acids from RVDVLQ to DDLYA. In the second, nucleotides 6316–6318 (CAG) is modified to the sequence CTC to change the encoded amino acid from Q to L. In the third, nucleotides 6613–6621 (TAC GCC TCC) is modified to the sequence CAC GCC TTC to change the encoded amino acids from YAS to HAF.

In either case, the resulting aglycone is bioconverted to 6-desmethyl erythromycin as described above although some modification for C-6 hydroxylation may be required. For example, the specificity of the native eryF gene product may need to be altered to accept the 6-desmethyl substrate or the use of a different P450 oxidase may be required.

Other starting materials include 6-hydroxy-erythromycin (where the methyl at C-6 has been replaced with a hydroxyl group), 6-oxo erythromycin (where the methyl at C-6 has been replaced with an oxo group), 6-methoxy erythromycin (where the methyl at C-6 has been replaced with a methoxy group) and 6-desmethyl, 7-hydroxy-erythromycin. In one embodiment, 6-OH, 6-OMe erythromcyins are made by replacing AT4 of 6-dEB or 8,8a-deoxyoleandolide synthase with an AT domain encoding hydroxymalonate or methoxymalonate. See PCT Publication WO 00/20601 which is incorporated herein by reference. The 6-OH and 6-OMe aglycone is bioconverted to 6-desmethyl-6-hydroxy erythromycin and 6-desmethyl-6-methoxy erythromycin respectively by fermentation with an appropriate eryA mutant that is incapable of producing 6-dEB and in which the eryF (C-6 hydroxylase) function has been deleted or otherwise inactivated. Fermentation of 6-OH or 6-OMe aglycone with an eryA mutant that possesses eryF (or equivalent) function lead to the 6-desmethyl-6-oxo erythromycin.

In one embodiment, 6-desmethyl, 7-hydroxy erythromycins are made by replacing AT4 of a 6-dEB or 8,8a-deoxyoleandolide polyketide synthase with a malonyl specific AT as described above as well as deleting or otherwise inactivating the dehydratase activity of module 3 ("DH3"). The resulting 6-desmethyl, 7-hydroxy aglycone is converted into the corresponding erythromycin derivative by fermentation with an appropriate eryA mutant that is incapable of producing 6-dEB as described above.

Synthetic Methods

The methods described herein are generally applicable to all erythromycins and erythromycin derivatives (e.g., erythromycins A, B, C, and D, 13-substituted erythromycins A, B, C, and, D, erythronolide B, 3-α-mycarosylerythronolide B, and derivatives thereof) unless explicitly limited. As such, references to specific embodiments are for the purposes of illustration only and are not intended to limit in any way the scope of the present invention.

In one aspect of the present invention, methods for forming the 8,9-anyhydro erythromycin 6,9-enol ether and 6,9 epoxide compounds are provided. The 8,9-anhydro erythromycin 6,9-enol ethers are also referred to as enol ethers or dihydrofurans. The 6,9-epoxides are also referred to as epoxides or tetrahydrofurans. Scheme 1A illustrates one embodiment for making the enol ether and epoxide compounds from erythromycin A and B derivatives (where $R^6$ is hydrogen or hydroxyl and $R^7$ is as previously described).

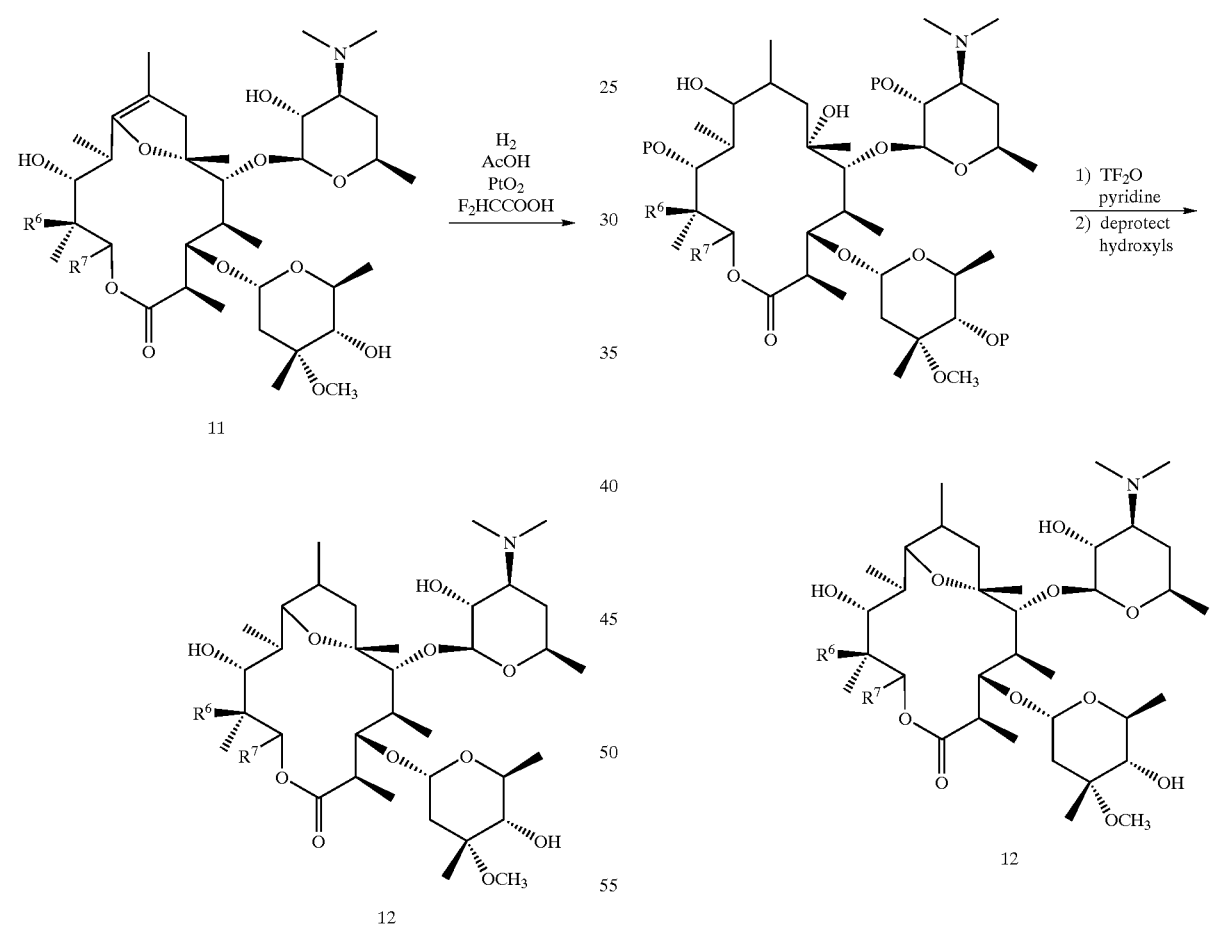

In general, the enol ether compounds 11 are formed by treating with mild acid the desired erythromycin starting material such as 10 (see Example 3). The corresponding epoxide 12 is formed by reducing the carbon-carbon double bond between C-8 and C-9 of the enol ether 11 (see Example 4). Scheme 1B illustrates another embodiment for making epoxide 12 also from compound 10.

The free hydroxyls of erythromycin 10 are protected and the C-9 ketone is reduced with sodium borohydride to a 9-dihydro erythromycin intermediate (where C-9 is —CHOH—). The hydroxyl group at C-9 is subsequently activated and displaced. The protecting groups are then removed to yield compound 12. Examples 12–17 describe this protocol in greater detail starting from erythromycins A and B (which are specific embodiments of compound 10) and their 4"-deoxy counterparts as starting material.

In another aspect of the present invention, methods for demethylating one or both of the 3'-N-methyl groups are provided. The demethylated 3'-nitrogen then may be subsequently reacted with an alkyl or an aryl group. The 3'-N demethylation and subsequent alkylation (or arylation) may be performed using erythromycins, enol ethers, or epoxide derivatives. Because these methods can be used on a wide variety of starting materials, the timing of these reactions is determined by the desired modifications at other macrolide positions. Scheme 2 illustrates one embodiment where the demethylation and alkylation reactions occur after the enol ether formation.

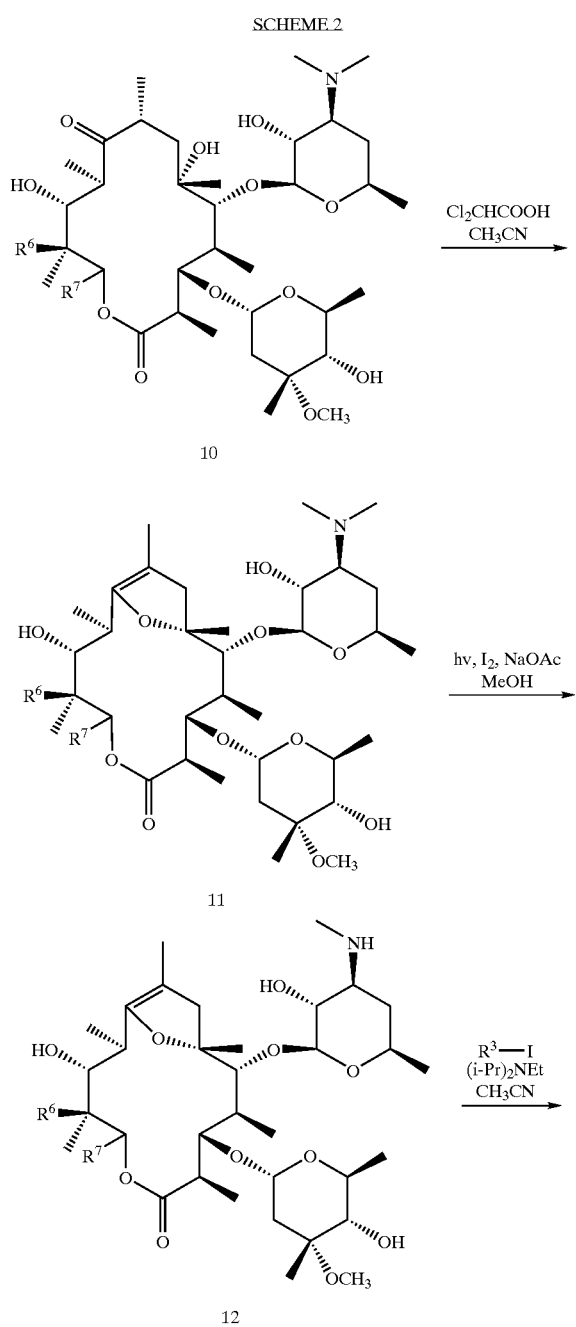

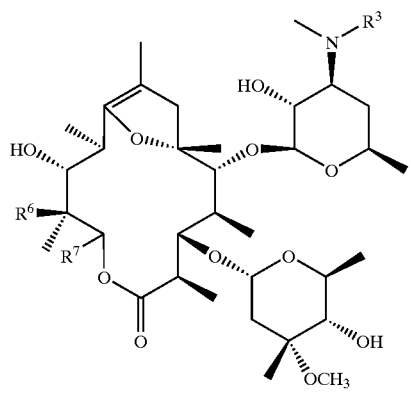

Enol ether 11, formed from erythromycin 10 as described previously by Scheme 1, is demethylated at the 3'-N by treatment with light, iodine and sodium acetate. Additional reagents and longer reaction times will remove both methyl groups if desired. The demethylated enol ether 12 is then alkylated or arylated with the appropriate alkyl halide or aryl halide to yield compound 13. Enol ether 13 may be optionally reduced to form its 6,9 epoxide counterpart using the procedures described by Scheme 1A. Examples 6 and 7 illustrate the demethylation and subsequent alkylation protocol with respect to erythromycin 10.

In another aspect of the present invention, methods for forming 11-oxo compounds are provided. Scheme 3 illustrates one embodiment with respect to 11-oxo-erythromycin A derivatives.

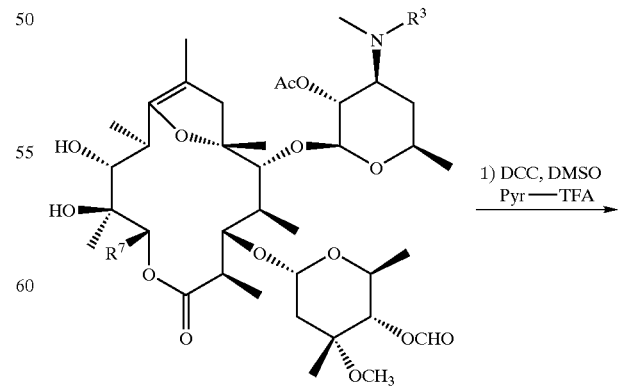

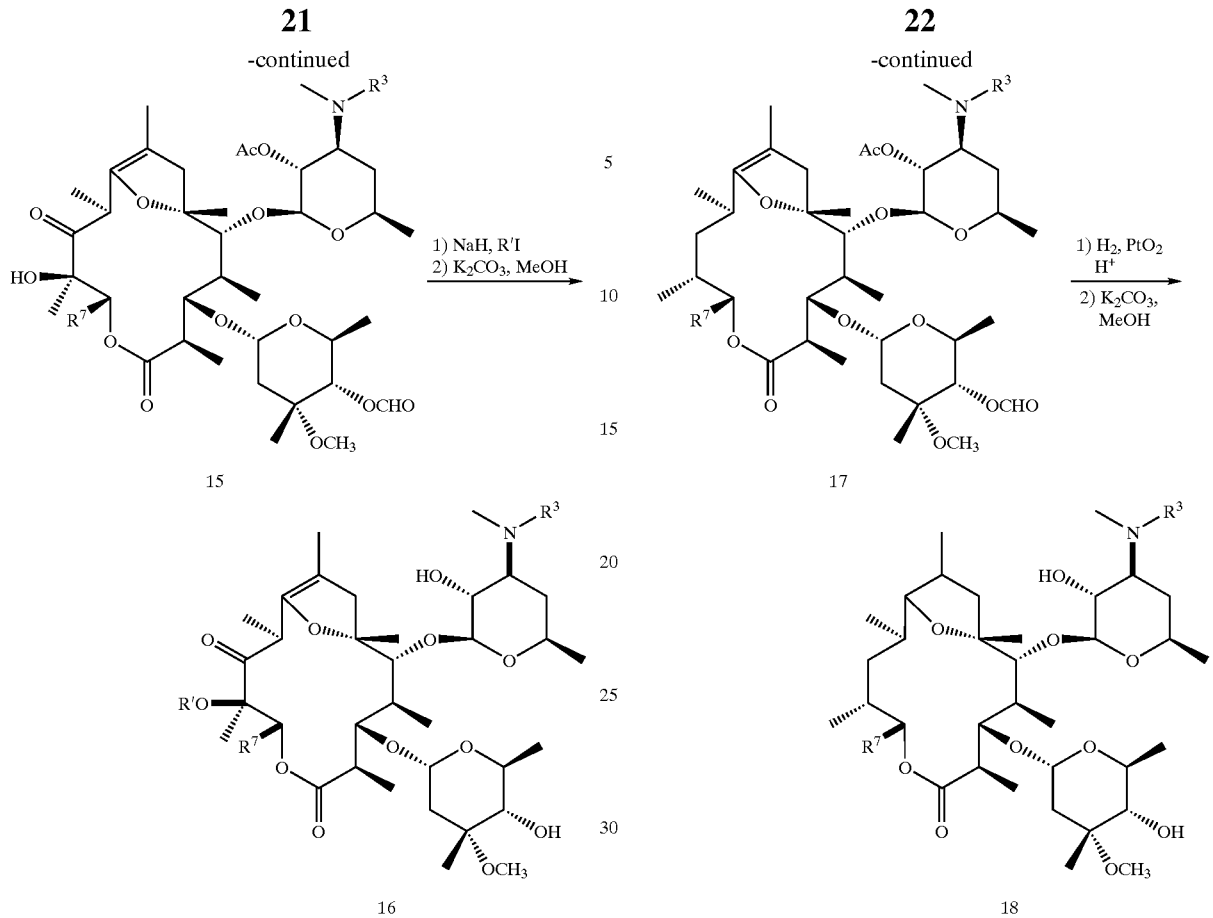

Enol ether 14, a 2' and 4" protected form of compound 13, is oxidized (e.g., using a carbodiimide and methylsulfoxide or a hypervalent iodine species) to yield compound 15. Deprotection at the 2' and 4" positions yields the unprotected form of compound 15. These protocols are described in greater detail in Examples 8–9. Alternatively, the hydroxyl at the C-12 position of compound 15 may be optionally alkylated to yield compound 16 after deprotection (see Example 10).

In another aspect of the present invention, methods for forming 11-hydrogen compounds are provided. Scheme 4 illustrates one embodiment for making 11 hydrogen counterparts from erythromycin B derivatives.

Compound 14a, the erythromycin B counterpart to compound 14 described in Scheme 3, is deoxygenated as described by Scheme 4 to yield compound 17. Deoxygenation of the 11-O-xanthate is illustrated, although other substrates such as the thiocarbonylimidazolide are also suitable intermediates. Compound 17 may be deprotected at the 2' and 4" positions to yield the unprotected form. Alternatively, as shown by Scheme 4, compound 17 may be reduced to yield the corresponding 6,9 epoxide 18 after deprotection.

In another aspect of the present invention, methods for making 4"-desoxy compounds are provided. Scheme 5 illustrates one embodiment.

SCHEME 4

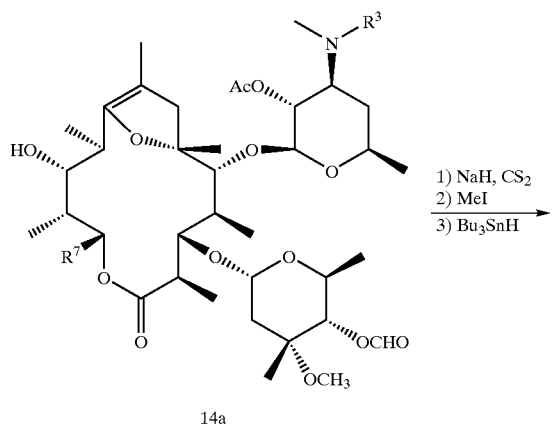

SCHEME 5

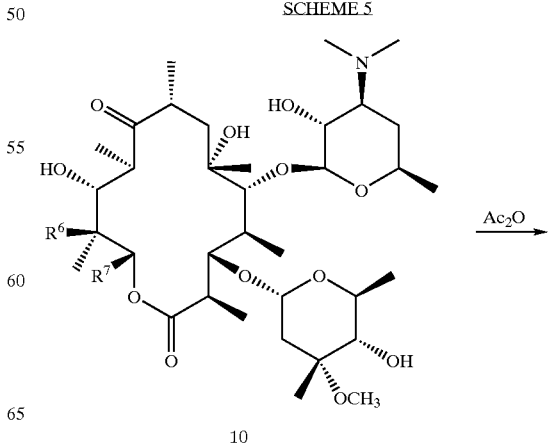

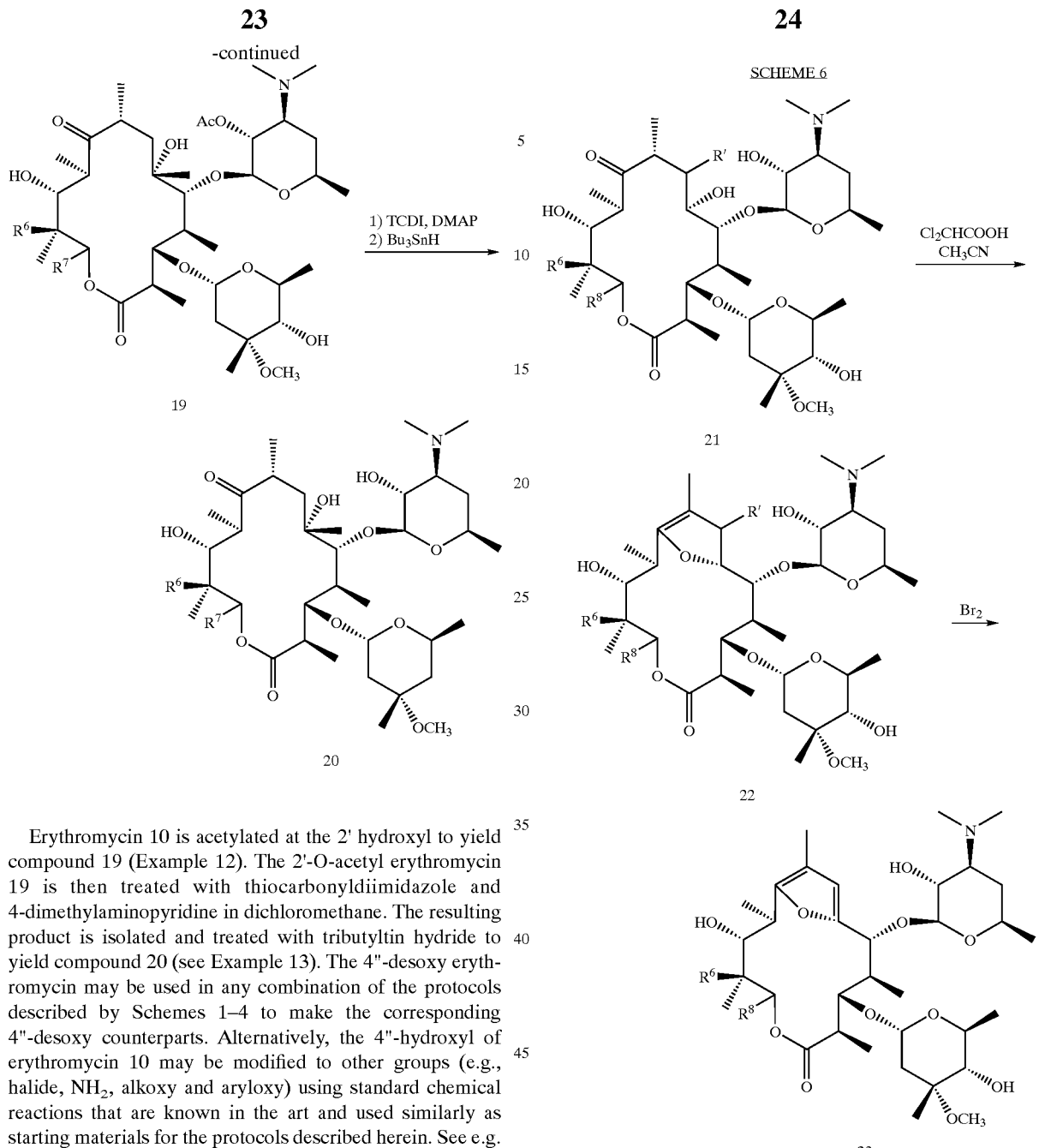

Erythromycin 10 is acetylated at the 2' hydroxyl to yield compound 19 (Example 12). The 2'-O-acetyl erythromycin 19 is then treated with thiocarbonyldiimidazole and 4-dimethylaminopyridine in dichloromethane. The resulting product is isolated and treated with tributyltin hydride to yield compound 20 (see Example 13). The 4"-desoxy erythromycin may be used in any combination of the protocols described by Schemes 1–4 to make the corresponding 4"-desoxy counterparts. Alternatively, the 4"-hydroxyl of erythromycin 10 may be modified to other groups (e.g., halide, $NH_2$, alkoxy and aryloxy) using standard chemical reactions that are known in the art and used similarly as starting materials for the protocols described herein. See e.g. Advanced Organic Chemistry 3rd Ed. by Jerry March (1985) which is incorporated herein by reference.

In another aspect of the present invention, methods for forming furanyl erythromycins are provided. In one embodiment, furanyl erythromycins are prepared synthetically by demethylating the naturally occurring methyl group at C-6. For example, a suitably protected erythromycin is converted to the 6-O-xanthate via reaction with carbon disulfide and methyl iodide, and the xanthate is pyrolyzed to yield 6,6a-anhydroerythromycin. Ozonolysis yields the 6-oxo-erythromycin, which can be converted to the 6,9-epoxide by dehydration from treatment with mild acid or acetic anhydride. Alternatively, the 6-oxo-erythromycin may be prepared recombinantly as described previously. Scheme 6 illustrates another embodiment using 6-desmethyl erythromycins.

6-Desmethyl erythromycin 21 (where $R^1$ and $R^6$ hydrogen or hydroxyl and $R^8$ is as previously described) is treated with mild acid such as dichloroacetic acid to form enol ether 22. Compound 22 is then treated with a mild oxidizing agent such as bromine in base to yield furanyl erythromycin 23. In yet another embodiment, 7-hydroxy-8,9-anhydro erythromycin 6,9-hemiacetal (22 where R' is hydroxyl, and $R^6$ is hydrogen or hydroxyl and $R^8$ is as previously described) is mesylated and subjected to base-catalyzed elimination to yield furanyl erythromycin 23.

In another aspect of the present invention, methods for forming 12-membered enol ethers are provided. Scheme 6 illustrates one embodiment for making these compounds.

SCHEME 7

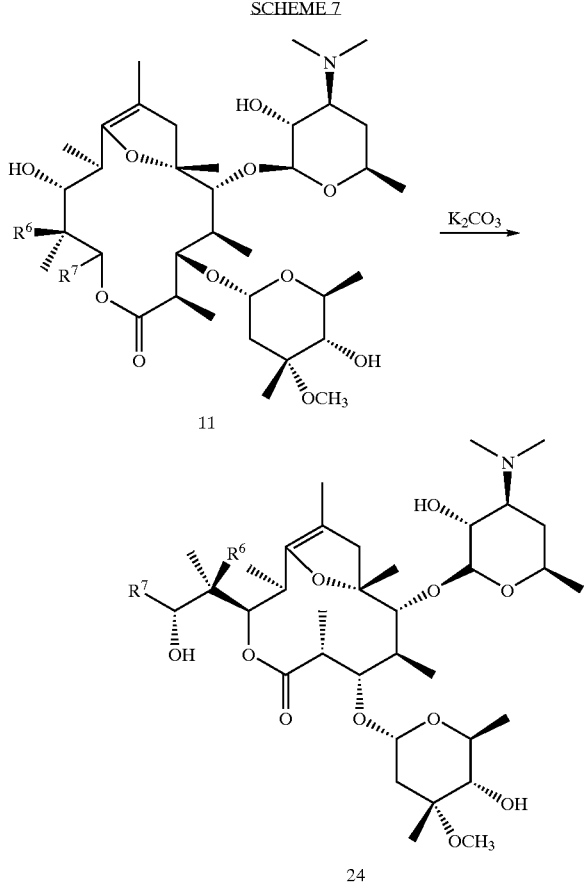

Erythromycin enol ether 11 is treated with potassium carbonate in methanol to yield the 12 membered enol ether 24 (see Example 5). A 12 membered 6,9 epoxide may be made using the same procedure by starting with the 6,9 epoxide form of erythromycin such as compound 12 instead of compound 11. A 12 membered furanyl compound can be made using the same procedure by starting with furanyl erythromycin 23 instead of compound 11.

Methods of Use

In general, methods of using the compounds of the present invention comprise administering to a subject in need thereof a therapeutically effective amount of a compound of the present invention. Illustrative examples of disorders that may be treated with the inventive compounds include but are not limited to gastroparesis, gastroesophageal reflux disease, anorexia, gall bladder stasis, postoperative paralytic ileus, scleroderma, intestinal pseudoobstruction, gastritis, emesis, and chronic constipation (colonic inertia).

The therapeutically effective amount can be expressed as a total daily dose of the compound or compounds of this invention and may be administered to a subject in a single or in divided doses. The total daily dose can be in amounts, for example, of from about 0.01 to about 25 mg/kg body weight, or more usually, from about 0.1 to about 15 mg/kg body weight. Single dose compositions may contain such amounts or submultiples thereof as to make up the daily dose. In general, treatment regimens according to the present invention comprise administration to a subject in need of such treatment of from about 10 mg to about 1000 mg of the compound(s) of the present invention per day in single or multiple doses.

Typically, the inventive compound will be part of a pharmaceutical composition or preparation which may be in any suitable form such as solid, semisolid, or liquid form. In general, the pharmaceutical preparation will contain one or more of the compounds of the invention as an active ingredient and a pharmaceutically acceptable carrier. Typically the active ingredient is in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. Oral dosage forms may be prepared essentially as described by Hondo et al., 1987, *Transplantation Proceedings XIX, Supp.* 6: 17–22, incorporated herein by reference.

The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

In summary, the present invention provides novel macrolide compounds, methods for making and methods of using the same which are further illustrated by the following examples.

EXAMPLE 1

Method of Making 13-propyl-6-deoxyerythronolide B (13-propyl-6-dEB

A 1 mL vial of the CH999/pJRJ2 (*Streptomyces coelicolor* that contains a PKS in which the ketosynthase domain of module 1 has been inactivated by mutation) working cell bank is thawed and the contents of the vial are added to 50 mL of Medium 1 in a 250 mL baffled flask.

Medium 1 comprises 45 g/L cornstarch; 10 g/L corn steep liquor; 10 g/L dried, inactivated brewers yeast; and 1 g/L $CaCO_3$. This solution is sterilized by autoclaving for 90 minutes at 121° C. After sterizilization, 1 mL/L of sterile filtered 50 mg/ml thiostrepton in 100% DMSO and 1 mL/L autoclaved 100% antifoam B silicon emulsion (J. T. Baker) are added prior to use.

The flask containing the thawed cells and Medium 1 is placed in an incubator/shaker maintained at 30±1° C. and 175±25 RPM for 48±10 hours. The 50 mL culture is then added to a 2.8 L baffled flask containing 500 mL of Medium 1. This flask is incubated in an incubator/shaker at 30±1° C. and 175±25 RPM for 48±10 hours. The 500 mL culture is than used to inoculate a 10 L fermenter containing 5 L of Medium 1. The fermenter is controlled at 30° C., pH 6.5 by addition of 2.5 N $H_2SO_4$ and 2.5 N NaOH, agitation rate 600 RPM, and air flow rate 1–2 LPM. Foam is controlled by the addition of a 50% solution of Antifoam B as needed. The fermenter culture is allowed to grow under these conditions for 24±5 hours.

A 150 L fermenter is prepared by sterilizing 100 L of Medium 1 at 121° C. for 45 minutes. After the growth period, the contents from the 10 L fermenter are aseptically added to a 150 L fermenter. The fermenter is controlled at 30° C., pH 6.5 by addition of 2.5 N $H_2SO_4$ and 2.5 N NaOH, dissolved oxygen ≧80% air saturation by agitation rate (500–700 RPM), air flow rate (10–50 LPM), and/or back pressure control (0.1–0.4 bar). Foam is controlled by the addition of a 50% solution of Antifoam B as needed.

At 35±5 hours, after dissolved oxygen has reached a minimum and $CO_2$ content in fermenter off gas has reached a maximum, (2S, 3R)-2-methyl-3-hydroxypentanoyl-N-acetylcysteamine (propyl diketide) is added to a final concentration of 2 g/L. Propyl diketide is prepared by solubolizing in dimethyl sulfoxide at a ratio of 2:3 (diketide to DMSO) and then filter sterilized (0.2 μm, nylon filter). Production of 13-propyl-6-deoxyerythonolide B (13-propyl-6-dEB) ceases on day 8 and the fermenter is harvested. The fermentation broth is centrifuged at 20,500 g in an Alpha Laval AS-26 centrifuge. The product is predominantly in the centrate; the centrifuged cell mass is discarded.

After centrifugation, solid phase extraction is performed using HP20 resin (Mitsubishi). Column size is selected based on centrate volume and titer, so that the loading capacity of 15 g 13-propyl-6-dEB per liter HP20 resin is not exceeded. The centrifuged broth is passed through the resin bed at a linear flow rate of 300±20 cm/h. The pressure on the column should not exceed 15 psi. The resin is then washed with 2 column volumes (CV) of water and then 2 CV of 30% methanol, each at a rate of 300±20 cm/h. 13-propyl-6-dEB is eluted using 7–10 CV 100% methanol at arate of 300±20 cm/h. During elution, fractions of ½ CV are collected. The fractions are then analyzed, and those containing product are combined to yield a product pool containing >95% of the original 13-propyl-6-dEB in the centrifuged broth. The product pool is reduced to solids using rotary evaporation. Product purity at this stage is 5–35%. Methanol-insoluble material is removed from the product pool by suspending the solids in 3 L 100% methanol per 100 L original broth volume, mixing for 20 minutes, and filtering.

The final purification step is chromatography using HP20SS resin (Mitsubishi). Column size is selected based on amount of product, so that the loading capacity of 15 g 13-propyl-6-dEB per liter HP20SS resin is not exceeded. The filtered methanol solution is diluted by adding an equal volume of water. The 50% methanol solution is passed through the resin bed at a linear flow rate of 300±20 cm/h. The column is then washed with 2 CV of 50% methanol at a rate of 300±20 cm/h. Product is eluted using 12 CV 70% methanol at a rate of 300±20 cm/h. During elution, fractions of ½ CV are collected. The fractions are then analyzed, and those containing >50 mg/L 13-propyl-6-dEB and having >20% chromatographic purity are combined. The product pool is reduced to solids using rotary evaporation. Product purity at this stage is >65% and is suitable for bioconversion to the appropriate erythromycin.

EXAMPLE 2
Method of Making 13-propyl erythromycin A

A 1 mL vial from working cell bank K39-14V (an eryA mutant of S. erythraea that is incapable of producing 6-dEB) is thawed and the contents of the vial are added to 50 mL of Medium 2 in a 250 mL baffled flask.

Medium 2 comprises 16 g/L cornstarch; 10 g/L corn dextrin; 15 g/L soy meal flour; 4 g/L $CaCO_3$; 5 g/L corn steep liquor; 6 g/L soy bean oil; 2.5 g/L NaCl; and 1 μL $(NH_4)_2SO_4$. This solution is sterilized by autoclaving for 60 minutes at 121° C. and 1 mL/L autoclaved 100% antifoam B silicon emulsion (J. T. Baker) is added prior to use.

The flask containing the thawed cells and Medium 2 is placed in an incubator/shaker maintained at 34±1° C. and 175±25 RPM for 48±10 hours. The 50 mL culture is then added to a 2.8 L baffled flask containing 500 mL of Medium 2. The flask is incubated in an incubator/shaker at 34±1° C. and 175±25 RPM for 48±10 hours. The 500 mL culture is than used to inoculate a 10 L fermenter containing 5 L of Medium 2. The fermenter is controlled at 34° C., pH 7.0 by addition of 2.5 N $H_2SO_4$ and 2.5 N NaOH, agitation rate 600 RPM, and air flow rate 1–2 LPM. Foam is controlled by the addition of a 50% solution of Antifoam B as needed. The fermenter culture is allowed to grow under these conditions for 24±5 hours.

A 150 L fermenter is prepared by sterilizing 100 L of Medium 3 at 121° C. for 45 minutes. Medium 3 comprises 17.5 g/L cornstarch; 16 g/L corn dextrin; 16.5 g/L soy meal flour; 4 g/L $CaCO_3$; 6 g/L corn steep liquor; 3 g/L soy bean oil; 3.5 g/L NaCl; and 1 g/L $(NH_4)_2SO_4$. After the growth period, the contents from the 10 L fermenter are aseptically transferred to the 150 L fermenter. The fermenter is controlled at 34° C., pH 7.0 by addition of 2.5 N $H_2SO_4$ and 2.5 N NaOH, dissolved oxygen ≧80% air saturation by agitation rate (500–700 RPM), air flow rate (15–50 LPM), and/or back pressure control (0.1–0.4 bar). Foam is controlled by the addition of a 50% solution of Antifoam B.

At 24±5 hours a 58–60 mL/hour 15% dextrin (w/v) feed is initiated. The dextrin solution is continuously mixed during the feed period. At 24±5 hours 25 grams of 13-propyl-6dEB are added to the fermenter. The 13-propyl-6dEB is prepared by solubolizing 25 grams of 13-propyl-6dEB in 400–600 mL of 100% ethanol and filtering (0.2 μm, nylon filter). Conversion of 13-propyl-6dEB to 13-propyl-erythromycin A ceases after 60±10 hours and the fermenter is harvested. The fermentation broth is centrifuged at 20,500 g in an Alpha Laval AS-26 centrifuge. The product is predominantly in the centrate; the centrifuged cell mass is discarded.

After centrifugation, solid phase extraction is performed using HP20 resin (Mitsubishi). Column size is selected based on centrate volume and titer, so that the loading capacity of 15 g 13-propyl-erythromycin A per liter HP20 resin is not exceeded. The centrifuged broth is adjusted to pH 9, then passed through the resin bed at a linear flow rate of 275±25 cm/h. The pressure on the column should not exceed 15 psi. The resin is then washed with 1 column volume (CV) of water at a rate of 275±25 cm/h. 13-propyl-6dEB is eluted using 5 CV 100% methanol at a rate of 275±25 cm/h. During elution, fractions of 1 CV are collected. The fractions are then analyzed, and those containing product are combined to yield a product pool. The product pool is reduced to solids using rotary evaporation.

Methanol-insoluble material is removed from the product pool by suspending the solids in 1 L 100% methanol per 100 L original broth volume, adjusting to pH 9, and filtering. The product pool (filtrate) is reduced to solids using rotary evaporation.

13-propyl-erythromycin A is extracted from the product pool (solids) by adding 2 L 4:1 hexane:acetone per 100 L original broth volume, mixing for 20 minutes, and filtering. The remaining solids are extracted the same way two more times and filtrates are combined. The product pool is reduced to solids using rotary evaporation.

The final purification step is chromatography using HP20SS resin (Mitsubishi). Column size is selected based on amount of product, so that the loading capacity of 15 g 13-propyl erythromycin A per liter HP20SS resin is not exceeded. The solids from the previous steps are dissolved in 1 L methanol per 100 L original broth volume, and an equal volume of water is added. The 50% methanol solution is passed through the resin bed at a linear flow rate of 275±25 cm/h. The column is then washed with 1 CV of 50% methanol, then 3 CV 60% methanol, each at a rate of 275±25 cm/h. Product is eluted using 3 CV 70% methanol, then 10

CV 75% methanol, each at a rate of 275±25 cm/h. During elution, fractions of ½ CV are collected. The fractions are then analyzed, and those containing 13-propyl-erythromycin A are combined. The product pool is reduced to solids using rotary evaporation.

EXAMPLE 3
8,9-anhydro-6,9-hemiacetal (enol ether) formation

A solution of erythromycin (100 mg) in anhydrous acetonitrile (2 mL) is treated with dichloroacetic acid (0.015 mL) under inert atmosphere until thin-layer chromatography reveals disappearance of starting material (2 days). The reaction mixture is concentrated, redissolved in 50 mL of dichloromethane, and washed with saturated $NaHCO_3$. The organic phase is dried over $Na_2SO_4$, filtered, and concentrated to give the crude product. Silica gel chromatography (acetone+2% $Et_3N$, hexanes) gives the pure product. Other compounds of the invention are formed by substituting the corresponding erythromycin derivative for the erythromycin in the above procedure.

An exemplary NMR data for one of the compounds of the present invention, 8,9-anhydroerythromycin A 6,9-hemiacetal is as follows. $^{13}C$-NMR ($CDCl_3$): δ178.2, 151.7, 102.9, 101.4, 94.6, 85.5, 80.1, 78.2, 78.1, 76.3, 75.3, 73.0, 70.8, 70.1, 68.8, 65.8, 65.6, 49.5, 44.7, 43.2, 42.6, 40.3, 34.6, 30.5, 28.7, 26.2, 21.5, 21.3, 21.0, 18.2, 16.1, 15.0, 13.4, 11.9, 11.4, 10.8, 8.6.

EXAMPLE 4
Hydrogenation of 8,9-anhydroerythromycin 6,9-hemiacetals to (8S,9R)-9-deoxo-6,9-epoxyerythromycins A solution of the 8,9-anhydroerythromycin 6,9-hemiacetal (0.55 mmol; Example 3) in 24 mL of glacial acetic acid is treated with difluoroacetic acid (0.1 mL) and platinum oxide (0.4 g). The mixture is shaken under 4 atm of hydrogen at ambient temperature for 3 hours, or until consumption of starting material as indicated by thin-layer chromatography. Ammonium acetate (0.3 g) is added, the mixture is stirred for 15 minutes, then filtered and concentrated. The residue is dissolved in dichloromethane, washed with sat. $NaHCO_3$, dried over $Na_2SO_4$, filtered, and evaporated. Silica gel chromatography (acetone+2% $Et_3N$, hexanes) gives the pure product.

EXAMPLE 5
Ring Contraction of 14-membered to 12-membered macrolides

A solution of the 8,9-anhydroerythromycin 6,9-hemiacetal derivative (1 mmol; Example 3) and potassium carbonate (200 mg) in methanol (50 mL) is heated at reflux until thin-layer chromatographic analysis reveals the reaction has reached equilibrium. The mixture is evaporated to dryness, then dissolved in $CH_2Cl_2$ and chromatographed on silica gel. Both 14-membered enol ethers and 9-deoxo-6,9-epoxides are converted into their 12-membered macrolide counterparts using this procedure. Those derivatives containing 2'-O-acetates, 4"-O-formates, 4"-O-(2,2,2-trichloroethoxycarbonyl), or 11,12-cyclic carbonates are deprotected during this process.

EXAMPLE 6
3'-N-desmethyl erythromycin derivatives

Sodium acetate trihydrate (300 mg) and iodine (116 mg) are added sequentially to a solution of erythromycin (300 mg) in 3 mL of methanol. The reaction mixture is exposed to a 120 W flood lamp and stirred until complete reaction is determined by thin-layer chromatographic analysis. Excess reagents are quenched by addition of saturated sodium thiosulfate solution, and the volatiles are removed under reduced pressure and the mixture is diluted with dichloromethane. The organic phase is washed with saturated $NaHCO_3$, dried over $Na_2SO_4$, filtered, and concentrated to give the crude product. Silica gel chromatography (acetone+2% $Et_3N$, hexanes) gives the pure product.

The 3'-N-desmethyl-8,9-anhydroerythromycin 6,9-hemiacetals are prepared by substituting the 8,9-anhydroerythromycin 6,9-hemiacetals for the erythromycin in the above procedure.

EXAMPLE 7
3'-N-desmethyl-3'-N-alkyl-erythromycin derivatives

A solution of the 3'-N-desmethyl-erythromycin derivative (0.5 mmol; Example 6) in acetonitrile (6 mL) is treated with diisopropylethylamine (0.23 mL) and the desired alkylating agent (0.6 mmol) and stirred at 40–80° C. under inert atmosphere until consumption of the erythromycin starting material as determined by thin-layer chromatographic analysis. The reaction mixture is concentrated under vacuum and redissolved in dichloromethane, washed with saturated $NaHCO_3$, dried over $Na_2SO_4$, filtered, and concentrated to give the crude product. Silica gel chromatography (acetone+2% $Et_3N$, hexanes) gives the pure product.

Alkylating agents useful in this procedure include ethyl iodide, benzyl bromide, 2-iodopropane, 4-bromo-1-butene, allyl bromide, propargyl bromide, or sec-butyl iodide, or the corresponding trifluoromethanesulfonates, which give rise to the 3'-N-ethyl, isopropyl, butenyl, allyl, propargyl, or sec-butyl derivatives, respectively.

3'-N-desmethyl-3'-N-alkyl-8,9-anhydroerythromycin 6,9-hemiacetal is prepared by substituting 3'-N-desmethyl-8,9-anhydroerythromycin 6,9-hemiacetal (Example 7) for the 3'-N-desmethyl-erythromycin in the above procedure.

EXAMPLE 8
2'-O-acetyl-4"-O-formyl-erythromycins

Step 1. 2',4"-di-O-formylerythromycin. To a stirred solution of the erythromycin (1 mmol) in ether (25 mL) and pyridine (0.5 mL) at 0° C., formic acetic anhydride (18 mmol) is added and the reaction mixture is stirred for 1 hr at 0° C. and 3 hr at 25° C. The reaction mixture is poured onto ice and the $Et_2O$ layer is washed with cold saturated $NaHCO_3$ solution, dried with sodium sulfate and concentrated at reduced pressure. The residue is then crystallized from ether or acetonitrile.

Step 2. 4"-O-formylerythromycin. To a solution of the 2',4"-di-O-formylerythromycin (1 mmol) in acetone (10 mL), saturated $NaHCO_3$ solution (10 mL) is added and the reaction mixture is stirred until deemed sufficiently complete by TLC analysis. The volatiles are removed at reduced pressure and the aqueous residue is extracted with methylene chloride. The organic layer is washed with water, dried with sodium sulfate and concentrated at reduced pressure. The residue is then crystallized from ether or acetonitrile.

Step 3. 2'-O-acetyl-4"-O-formylerythromycin. To a solution of the 4"-O-formylerythromycin A (1 mmol) in methylene chloride (25 mL) at 0° C., acetic anhydride (1.1 mmol) is added and the reaction mixture is stirred overnight. The excess reagents are quenched by addition of saturated $NaHCO_3$ solution. The organic layer is dried with magnesium sulfate, concentrated under reduced pressure and the residue is recrystallized from acetonitrile.

EXAMPLE 9
11-keto erythromycins

To a solution of 2'-O-acetyl-4"-O-formylerythromycin 6,9-enolether (Example 8, 1 mmol), methylsulfoxide (11 mmol), and dicyclohexylcarbodiimide (3 mmol) in methylene chloride (13 mL) at 0° C., pyridinium trifluoroacetate (3 mmol) is added dropwise. The reaction mixture is stirred 4 hr at room temperature and filtered. The filtrate is washed with water, dried with sodium sulfate and concentrated at reduced pressure. The residue is purified by flash chromatography.

EXAMPLE 10
12-O-alkyl-11-keto erythromycins

To a solution of 2'-O-acetyl-4"-O-formyl-11-deoxy-11-oxoerythromycin 6,9-enolether (Example 9, 1 mmol) in dimethylformamide (15 mL) at 0° C., sodium hydride (1.5 mmol) is added and the reaction mixture is stirred for 20 min. The alkylating agent (e.g., iodomethane to produce 12-O-methyl) (2 mmol) is then added and the reaction mixture is stirred for 2 hr or until deemed complete by TLC. The excess reagents are quenched by addition of saturated $NaHCO_3$ solution and the mixture extracted with ethyl acetate. The combined organic layers are washed with water and brine, then dried with sodium sulfate and concentrated at reduced pressure. The residue is then dissolved in methanol (7.5 mL), saturated $NaHCO_3$ solution (0.5 mL) is added and the reaction mixture is stirred overnight. The reaction mixture is extracted with methylene chloride and the combined organic layers are washed with brine and concentrated at reduced pressure. The residue is purified by flash chromatography.

EXAMPLE 11
11-deoxyerythromycin B 6,9-enolether

A 0° C. solution of 2'-O-acetyl-4"-O-formylerythromycin B 6,9-enolether in THF under an inert atmosphere is treated with 60% sodium hydride and stirred for 30 minutes and allowed to warm to ambient temperature. Carbon disulfide is then added, the reaction mixture is stirred for 1 hour and methyl iodide is added and stirred for an additional hour. The excess reagents are quenched by addition of saturated sodium bicarbonate solution and the volatiles removed under reduced pressure. The aqueous residue is extracted with methylene chloride and the combined organic layers are washed with saturated sodium bicarbonate solution, dried with sodium sulfate, and concentrated under reduced pressure to give the crude product which is dissolved in toluene and heated to reflux under an inert atmosphere. Tributyltin hydride and AIBN are then added and the reaction mixture is kept at reflux temperature for 1 hour and allowed to cool to room temperature. The volatiles are removed at reduced pressure, the residue is dissolved in acetonitrile and then washed repeatedly with hexane. The acetonitrile layer is concentrated under reduced pressure. The residue is purified by flash chromatography and dissolved in methanol, saturated $NaHCO_3$ solution (3% by volume) is added and the reaction mixture is stirred overnight. The reaction mixture is extracted with methylene chloride and the combined organic layers are washed with brine and concentrated at reduced pressure. The residue is purified by flash chromatography.

EXAMPLE 12
2'-O-acetyl-erythromycin

A 0° C. solution of erythromycin (13.4 mmol) in ethyl acetate (50 mL) is treated with acetic anhydride (1.4 mL) for 30 minutes, then kept for 4 hours at ambient temperature. The mixture is quenched with sat. $NaHCO_3$, and extracted with ethyl acetate. The extracts are combined, dried over MgSO4, filtered, and concentrated to dryness under reduced pressure to yield the crude product. The product is either crystallized or purified by silica gel chromatography. NMR data follows for one of the compounds of the present invention, 2'-O-acetyl-13-propyl erythromycin A, that was crystallized from acetonitrile. $^{13}$C-NMR ($CDCl_3$): δ222.3, 175.4, 170.0, 100.9, 96.1, 83.4, 79.7, 75.1, 75.0, 74.5, 72.7, 71.7, 68.9, 68.4, 65.7, 63.6, 49.4, 45.2, 44.8, 40.7, 39.2, 38.1, 37.8, 35.0, 31.6, 30.3, 30.2, 27.0, 22.6, 21.5, 21.5, 21.2, 19.5, 18.6, 18.1, 16.3, 15.8, 14.1, 14.0, 12.0, 9.0.

EXAMPLE 13
2'-O-acetyl-4"-deoxy-erythromycin

Step 1. A mixture of 2'-O-acetyl-erythromycin (3.5 mmol; Example 12), thiocarbonyldiimidazole (1 g), and 4-dimethylaminopyridine (0.67 g) in 100 mL of $CH_2Cl_2$ is stirred overnight at ambient temperature. The mixture is treated with 150 mL of sat. $NaHCO_3$, and the organic phase is then washed with water, dried over $MgSO_4$, filtered, and evaporated. The product 4"-O-thiocarbonylimidazolide is crystallized.

Step 2. The product from Step 1 is dissolved in 60 mL of toluene and heated to 98° C. Tributyltin hydride (1.9 mL) is added followed by 2,2'-azobisisobutyronitrile (60 mg) and heating is continued for 35 minutes. The mixture is concentrated under reduced pressure. The oily residue is dissolved in 340 mL of acetonitrile, washed with 5 portions of hexanes, and concentrated to yield the crude product. Purification by silica gel chromatography yields the pure product. NMR data follows for one of the compounds of the present invention, 2'-O-acetyl-4"-deoxyerythromycin A: $^{13}$C-NMR: δ222.0, 175.6, 170.0, 100.4, 96.8, 83.2, 79.0, 74.8, 74.6, 71.7, 70.5, 68.9, 67.9, 63.2, 61.4, 49.2, 45.3, 45.1, 44.7, 40.7, 38.9, 37.9, 34.1, 30.7, 26.8, 25.5, 25.2, 22.2, 21.9, 21.5, 21.2, 18.2, 16.3, 15.9, 12.0, 10.6, 9.1.

EXAMPLE 14
2'-O-acetyl-4"-O-(2,2,2,-trichloroethoxycarbonyl)-erythromycin

A solution of 2'-O-acetyl-erythromycin (100 mmol; Example 12) and 4-dimethylaminopyridine (49.0 g) in $CH_2Cl_2$ (500 mL) is cooled to −78° C. and stirred under inert atmosphere. Trichloroethyl chloroformate (50 mL) is added dropwise, and the mixture is stirred for 48 hours. After warming to ambient temperature, the mixture is washed with cold phosphate buffer (1:1 v/v mix of 5% $KH_2PO_4$ and 1% $K_2HPO_4$) followed by brine, dried over $MgSO_4$, filtered, and concentrated. The product is purified by crystallization or silica gel chromatography.

EXAMPLE 15
2'-O-acetyl-erythromycin A 11,12-cyclic carbonate

A mixture of 2'-O-acetyl-4"-deoxy-erythromycin A (1.6 mmol; Example 13), 1,1-carbonyldiimidazole (1.64 g), and 4-dimethylaminopyridine (0.41 g) in 13 mL of $CH_2Cl_2$ is warmed gently to dissolve the solids, then allowed to stir overnight at ambient temperature. Saturated $NaHCO_3$ (20 mL) is added and stirred for 15 minutes, then the mixture is extracted with $CH_2Cl_2$. The extract is washed with water, dried over $MgSO_4$, filtered, and evaporated to yield 2'-O-acetyl-4"deoxy-erythromycin A 11,12-cyclic carbonate.

2'-O-acetyl-4"-O-(2,2,2-trichloroethoxycarbonyl) erythromycin A 11,12-cyclic carbonate is made by substituting 2'-O-acetyl-4"-O-2,2,2-trichloroethoxycarbonyl)-erythromycin A (Example 14) for 2'-O-acetyl-4"-deoxy-erythromycin A in the above procedure.

EXAMPLE 16
(9S)-9-dihydro-erythromycins

A solution of 2'-O-acetyl-4"-deoxy-erythromycin A 11,12-cyclic carbonate (0.5 mmol; Example 15) in 10 mL of ethanol is treated with sodium borohydride (200 mg), and the reaction is monitored by thin-layer chromatography. When the reaction is ca. 80% complete, 0.5 M phosphate buffer (50 mL) is added and the mixture is extracted with $CH_2Cl_2$. The extract is washed with phosphate buffer, dried over $MgSO_4$, filtered, and evaporated. The product, (9S)-2'-O-acetyl-4"-deoxy-9-dihydro-erythromycin A 11,12-cyclic carbonate, is purified by silica gel chromatography. NMR data follows for one of the compounds of the invention, (9S)-2'-O-acetyl-9-dihydroerythromycin A 11,12-cyclic carbonate: $^{13}$C-NMR: δ175.8, 169.9, 153.8, 100.1, 96.7, 85.3, 82.3, 81.1, 80.0, 77.7, 76.5, 74.6, 71.7, 70.6, 68.6, 62.9, 61.8, 49.1, 45.3, 44.7, 42.3, 40.7, 34.5, 34.2, 33.6, 30.9, 25.5, 25.1, 22.9, 21.5, 21.4, 21.0, 20.1, 14.5, 14.4, 14.3, 10.7, 9.2.

(9S)-2'-O-acetyl-9-dihydro-erythromycin A is made by substituting 2'-O-acetyl-4"-O-(2,2,2-trichloroethyoxycarbonyl)-erythromycin A 11, 12-cyclic carbonate (Example 15) instead of 2'-O-acetyl-4"-deoxy-erythromycin A 11, 12-cyclic carbonate.

(9S)-2'-O-acetyl-4"-desoxy-9-dihydro-erythromycin B is made by substituting 2'-O-acetyl-4"-desoxy-erythromycin B (Example 13) instead of 2'-O-acetyl-4"-deoxy-erythromycin A 11, 12-cyclic carbonate.

(9S)-2'-O-acetyl-9-dihydro-erythromycin B is made by substituting 2',4",11-tri-O-acetyl erythromycin B (Example 20) instead of 2'-O-acetyl-4"-deoxy-erythromycin A 11, 12-cyclic carbonate.

EXAMPLE 17
9-deoxo-6,9-epoxy-erythromycins

A solution of (9S)-2'-O-acetyl-4"-deoxy-9-dihydro-erythromycin A 11,12-cyclic carbonate (1 mmol; Example 16) in 25 mL of $CH_2Cl_2$ at 0° C. is treated with pyridine (0.26 mL; Example 21) and trifluoromethanesulfonic anhydride (0.35 mL). After 30 minutes, sat. $NaHCO_3$ is added and the mixture is extracted with $CH_2Cl_2$. The extract is washed with water, dried over $MgSO_4$, filtered, and evaporated. The product, (8R,9R)-2'-O-acetyl-4"-deoxy-9-deoxo-6,9-epoxy-13-desethyl-13-R-erythromycin A, is isolated by silica gel chromatography.

EXAMPLE 18
Removal of 2'-O-acetate and 11,12-cyclic carbonate protection

A solution of the 2'-O-acetyl-erythromycin 11, 12-cyclic carbonate (1 mmol; Example 15) in 25 mL of methanol is treated with potassium carbonate (3 mmol). Upon completion of the reaction, the mixture is evaporated, and the residue is dissolved in $CH_2Cl_2$. The extract is washed with water, dried over $MgSO_4$, filtered, and evaporated. The product is isolated by silica gel chromatography.

EXAMPLE 19
Removal of 4"-O-(2,2,2-trichloroethoxycarbonyl) Protection

Samarium iodide is prepared by stirring a solution of samarium (3.43 mmol) and iodine (3.09 mmol) in 40 mL of tetrahydrofuran at reflux for 2.5 hours. Upon cooling to ambient temperature, 10 mg of $NiI_2$ is added and the mix is cooled to −78° C. A solution of the 4"-O-(2,2,2-trichloroethoxycarbonyl)-protected erythromycin derivative (0.386 mmol) in 10 mL of tetrahydrofuran is added, and the mix is stirred for 1 hour at −78° C. The reaction is quenched by addition of sat. $NaHCO_3$, warmed to ambient temperature, and extracted with ether. The extract is dried over $MgSO_4$, filtered, and evaporated. The product is purified by silica gel chromatography.

EXAMPLE 20
2',4", 11-tri-O-acetyl-erythromycins

A solution of erythromycin B (100 mmol), pyridine (500 mmol) and 4-dimethylaminopyridine (49.0 g) in $CH_2Cl_2$ (500 mL) is cooled on ice and stirred under inert atmosphere. Acetic anhydride (50 mL) is added dropwise, and the mixture is stirred for 48 hours. After warming to ambient temperature, the mixture is washed with cold phosphate buffer (1:1 v/v mix of 5% $KH_2PO_4$ and 1% $K_2HPO_4$) followed by brine, dried over $MgSO_4$, filtered, and concentrated. The product is purified by crystallization or silica gel chromatography.

EXAMPLE 21
Motilin Receptor Competitive Binding Assay

The compounds of the present invention are tested using a motilin receptor competitive binding assay. An illustrative protocol for such assay is described by Bormans et al, Regul. Peptides, 15: 143 (1986) which is incorporated herein by reference. In general, membranes prepared from rabbit antrum or duodenum are incubated with 25–50 pM $^{125}$I-labeled motilin and varying concentration of a test ligand. Protein-bound radioactivity is estimated from parallel reactions to which 100 nm unlabelled motilin is added. Efficacy of a test compound is expressed as $IC_{50}$ (M), the concentration of the test compound to reduce the specific binding capacity to 50%.

EXAMPLE 22
Contractile Activity Assay

The compounds of the present invention are tested in a contractile activity assay described by Depoortere et al, Peptides, 11:515–519 (1990) which is incorporated herein by reference. Briefly, integral segments of rabbit small intestine (1.5–2 cm) are vertically suspended in tissue baths (10 ml), continuously gassed with 95% oxygen, 5% carbon dioxide, and kept at 37° C. The tissue baths contain Hepes buffer (pH 7.4) comprising 137 mM NaCl; 5.9 mM KCl; 1.2 mM $CaCl_2$; 1.2 mM $MgCl_2$; 11.6 mM Hepes; and 11.5 mM glucose. Contractions are recorded isotonically. Cumulative concentrations response curves are established by adding logarithmically increasing doses of the test compounds in 100 μl quantities to the bath. From each curve, the negative logarithm of the concentration necessary to induce 50% of the maximal contraction ($pED_{50}$) is determined by fitting a sigmoid curve to the data.

What is claimed is:
1. A compound of the formula

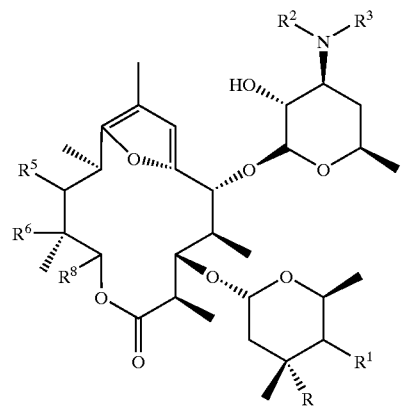

wherein:

R is hydroxyl or methoxy;

$R^1$ is selected from the group consisting of hydrogen, hydroxyl, halide, $NH_2$, $OR^9$,

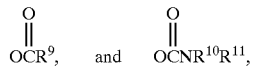

where $R^9$ is $C_{1-10}$ alkyl, $C_{2-10}$ alkenyl, $C_{2-10}$ alkynyl, aryl or heteroaryl and $R^{10}$ and $R^{11}$ are each independently hydrogen, $C_{1-10}$ alkyl, $C_{2-10}$ alkenyl, $C_{2-10}$ alkynyl, or aryl;

$R^2$ and $R^3$ are each independently selected from the group consisting of hydrogen, $C_{1-10}$ alkyl, $C_{2-10}$ alkenyl, $C_{2-10}$ alkynyl, aryl, alkylaryl, alkenylaryl, alkynylaryl or $R^2$ and $R^3$ together form a cycloalkyl or a cycloaryl moiety;

$R^5$ is hydrogen, hydroxyl, oxo, or together with $R^6$ and the carbons to which they are attached form a cyclic carbonate;

$R^6$ is hydrogen, hydroxyl, $OR^{12}$ where $R^{12}$ is $C_{1-10}$ alkyl, $C_{2-10}$ alkenyl, $C_{2-10}$ alkynyl, or together with $R^5$ and the carbons to which they are attached form a cyclic carbonate; and $R^8$ is $C_{1-10}$ alkyl, $C_{2-10}$ alkenyl, $C_{2-10}$ alkynyl, aryl, alkylaryl, alkenylaryl, alkynylaryl, amidoalkylaryl, amidoalkenylaryl, or amidoalkynylaryl.

2. The compound as in claim 1 wherein

R is hydroxyl or methoxy;

$R^1$ is hydrogen or hydroxyl;

$R^2$ and $R^3$ are each independently $C_{1-5}$ alkyl, phenyl, or benzyl;

$R^5$ is hydrogen, hydroxyl, or oxo;

$R^6$ is hydrogen, hydroxyl, or $C_{1-5}$ alkoxy; and $R^8$ is $C_{1-5}$ alkyl, $C_{2-5}$ alkenyl, $C_{2-5}$ alkynyl, aryl, alkylaryl, alkenylaryl, or alkynylaryl.

3. A compound according to claim 1, wherein

R is hydroxyl or methoxy;

$R^1$ is hydrogen or hydroxyl;

$R^2$ is methyl;

$R^3$ is methyl, ethyl, propyl, isopropyl, butyl, isobutyl, secbutyl or tertbutyl;

$R^5$ is hydrogen, hydroxyl, or oxo;

$R^6$ is hydrogen, hydroxyl, or methoxy; and $R^8$ is methyl, ethyl, vinyl, propyl, isobutyl, pentyl, prop-2-enyl, propargyl, but-3-enyl, 2-azidoethyl, 2-fluoroethyl, 2-chloroethyl, cyclohexyl, phenyl, or benzyl.

4. A compound according to claim 2, wherein

R is methoxy;

$R^1$ is hydroxyl;

$R^2$ is methyl;

$R^3$ is ethyl or isopropyl;

$R^5$ and $R^6$ are each hydroxyl; and $R^8$ is ethyl.

5. A method of treating a subject suffering from impaired GI motility comprising administering to a subject in need thereof a composition comprising a compound according to claim 1.

6. A method according to claim 5, wherein the subject is a human suffering from gastroparesis, gastroesophageal reflux disease, anorexia, gall bladder stasis, postoperative paralytic ileus, scleroderma, intestinal pseudoobstruction, gastritis, emesis, or chronic constipation (colortic inertia).

* * * * *